United States Patent
Wada et al.

(10) Patent No.: US 11,306,320 B2
(45) Date of Patent: Apr. 19, 2022

(54) METHOD FOR PROMOTING HOMOLOGOUS RECOMBINATION

(71) Applicant: Kao Corporation, Tokyo (JP)

(72) Inventors: Mayumi Wada, Wakayama (JP); Shintaro Ryo, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/465,697

(22) PCT Filed: Nov. 27, 2017

(86) PCT No.: PCT/JP2017/042326
§ 371 (c)(1),
(2) Date: Dec. 18, 2020

(87) PCT Pub. No.: WO2018/105420
PCT Pub. Date: Jun. 14, 2018

(65) Prior Publication Data
US 2020/0017867 A1    Jan. 16, 2020

(30) Foreign Application Priority Data

Dec. 7, 2016   (JP) .............................. JP2016-237757

(51) Int. Cl.
*C12N 15/82*    (2006.01)
*C12N 1/12*     (2006.01)
*C12N 15/90*    (2006.01)
*C12R 1/89*     (2006.01)

(52) U.S. Cl.
CPC ........... *C12N 15/8213* (2013.01); *C12N 1/12* (2013.01); *C12N 1/125* (2021.05); *C12N 15/902* (2013.01); *C12R 2001/89* (2021.05)

(58) Field of Classification Search
None
See application file for complete search history.

(56) References Cited

U.S. PATENT DOCUMENTS

| | | |
|---|---|---|
| 2008/0138905 A1 | 6/2008 | Inoue |
| 2009/0011508 A1 | 1/2009 | Takahashi et al. |
| 2013/0102040 A1 | 4/2013 | Radakovits et al. |
| 2017/0073711 A1 | 3/2017 | Iwai et al. |
| 2017/0335354 A1 | 11/2017 | Ozaki |

FOREIGN PATENT DOCUMENTS

| | | |
|---|---|---|
| JP | 2005-218402 A | 8/2005 |
| JP | 2007-222055 A | 9/2007 |
| JP | 2015-100327 A | 6/2015 |
| WO | WO 2005/083090 A1 | 9/2005 |
| WO | WO 2015/137449 A1 | 9/2015 |
| WO | WO 2016/076231 A1 | 5/2016 |

OTHER PUBLICATIONS

Tamura et al. (2002) Plant J 29(6):771-81.*
Walker et al. (2001) Nature 412:607-14.*
Takahashi et al. (2006) Mod Gen Genom 275:460-70.*
Al-Hoqani et al. (2016) Persp Phycol (https://doi.org/ 10.1127/ pip/ 2016/0065).*
Kilian et al. (2011) Proc Natl Acad Sci USA 108(52):21265-69.*
Li et al. (2104) Biosci Biotech Bichem 78(5):812-17.*
International Search Report (ISR) for PCT/JP2017/042326; I.A. fd Nov. 27, 2017, dated Feb. 20, 2018 from the Japan Patent Office, Tokyo, Japan.
International Preliminary Report on Patentability (IPRP), Chapter I of the Patent Cooperation Treaty, including the Written Opinion for PCT/JP2017/042326; I.A. fd Nov. 27, 2017, dated Jun. 11, 2019, by the International Bureau of WIPO, Geneva, Switzerland.
Kilian, O et al., "High-efficiency homologous recombination in the oil-producing alga *Nannochloropsis* sp.," Proc Natl Acad Sci U S A. Dec. 27, 2011;108(52):21265-9. doi: 10.1073/pnas.1105861108. Epub Nov. 28, 2011.
Ochi, T et al., "DNA repair. PAXX, a paralog of XRCC4 and XLF, interacts with Ku to promote DNA double-strand break repair," Science. Jan. 9, 2015;347(6218):185-188. doi: 10.1126/science.1261971.
Abdel-Banat, BMA et al., "Random and targeted gene integrations through the control of non-homologous end joining in the yeast *Kluyveromyces marxianus*," Yeast. Jan. 2010;27(1):29-39. doi: 10.1002/yea.1729.
Koh, CMJ et al., "Molecular characterization of KU70 and KU80 homologues and exploitation of a KU70-deficient mutant for improving gene deletion frequency in *Rhodosporidium toruloides*," BMC Microbiol. Feb. 27, 2014;14:50. doi: 10.1186/1471-2180-14-50.
Full=X-ray repair cross-complementing protein 6, Uniprot [online], accession No. W7TQ51, May 11, 2016, uploaded, [retrieved on Feb. 5, 2018], retrieved from the Internet: <URL: http://www.uniprot.Org/uniprot/W7TQ51.txt?version=9>.
Notice of Reasons for Refusal, drafted Apr. 9, 2021 and dated Apr. 27, 2021 for JP Patent Application No. 2016-237757, the Japan Patent Office, Tokyo, Japan.

(Continued)

*Primary Examiner* — Russell T Boggs
(74) *Attorney, Agent, or Firm* — Sterne, Kessler, Goldstein & Fox P.L.L.C.

(57) ABSTRACT

A method of producing a transformant, which contains using an alga belonging to the genus *Nannochloropsis* as a host, wherein function of the following protein (A) or (B) of the alga is suppressed, inhibited or deleted:

(A) a protein consisting of the amino acid sequence set forth in SEQ ID NO: 50; and
(B) a DNA binding protein consisting of an amino acid sequence having 70% or more identity with the amino acid sequence of the protein (A).

15 Claims, 2 Drawing Sheets

Specification includes a Sequence Listing.

(56) References Cited

OTHER PUBLICATIONS

UniProtKB/TrEMBL W7TQ51_9STRA, sequence version 1 (Apr. 16, 2014), entry version 9 (May 11, 2016), X-ray repair cross-complementing protein 6, Accession No. W7TQ51, May 11, 2016 uploaded, [retrieved on Feb. 5, 2018], Internet, URL http://www.uniprot.org/uniprot/W7TQ51.txt.
Jinkerson RE, et al.. "Genomic insights from the oleaginous model alga *Nannochloropsis gaditana*." Bioengineered. Jan.-Feb., 2013;4(1):37-43. doi: 10.4161/bioe.21880. Epub Aug. 24, 2012. PMID: 22922732; PMCID: PMC3566019.

* cited by examiner

Pvcp1-aphVIII-Tvcp1: Cassette fragment for paromomycin resistance gene expression

SEQUENCE LISTING

<160> NUMBER OF SEQ ID NOS: 51

<210> SEQ ID NO 1
<211> LENGTH: 375
<212> TYPE: DNA
<213> ORGANISM: Artificial Sequence
<220> FEATURE:

<223> OTHER INFORMATION: Zeocin resistance gene

<400> SEQUENCE: 1

| | | | | | | |
|---|---|---|---|---|---|---|
| atggccaagc | tgaccagcgc | cgttccggtg | ctcaccgcgc | gcgacgtcgc | cggagcggtc | 60 |
| gagttctgga | ccgaccggct | cgggttctcc | cgggacttcg | tggaggacga | cttcgccggt | 120 |
| gtggtccggg | acgacgtgac | cctgttcatc | agcgcggtcc | aggaccaggt | ggtgccggac | 180 |
| aacaccctgg | cctgggtgtg | ggtgcgcggc | ctggacgagc | tgtacgccga | gtggtcggag | 240 |
| gtcgtgtcca | cgaacttccg | ggacgcctcc | gggccggcca | tgaccgagat | cggcgagcag | 300 |
| ccgtggggc | gggagttcgc | cctgcgcgac | ccggccggca | actgcgtgca | cttcgtggcc | 360 |
| gaggagcagg | actaa | | | | | 375 |

<210> SEQ ID NO 2
<211> LENGTH: 48
<212> TYPE: DNA
<213> ORGANISM: Artificial Sequence
<220> FEATURE:
<223> OTHER INFORMATION: Primer No. 2

<400> SEQUENCE: 2
ccctccgagc agattatggc caagctgacc agcgccgttc cggtgctc        48

<210> SEQ ID NO 3
<211> LENGTH: 49
<212> TYPE: DNA
<213> ORGANISM: Artificial Sequence
<220> FEATURE:
<223> OTHER INFORMATION: Primer No. 3

<400> SEQUENCE: 3
ctcttccaca gaagcttagt cctgctcctc ggccacgaag tgcacgcag        49

<210> SEQ ID NO 4
<211> LENGTH: 32
<212> TYPE: DNA
<213> ORGANISM: Artificial Sequence
<220> FEATURE:
<223> OTHER INFORMATION: Primer No. 4

<400> SEQUENCE: 4
ggcggtcttt tgtcctttcc tctatagccc gc        32

<210> SEQ ID NO 5
<211> LENGTH: 31
<212> TYPE: DNA
<213> ORGANISM: Artificial Sequence
<220> FEATURE:
<223> OTHER INFORMATION: Primer No. 5

<400> SEQUENCE: 5
aatctgctcg aggggagga tcaagggaaa g        31

<210> SEQ ID NO 6
<211> LENGTH: 35
<212> TYPE: DNA
<213> ORGANISM: Artificial Sequence
<220> FEATURE:
<223> OTHER INFORMATION: Primer No. 6

<400> SEQUENCE: 6
gcttctgtgg aagagccagt ggtagtagca gtagc        35

<210> SEQ ID NO 7
<211> LENGTH: 34
<212> TYPE: DNA
<213> ORGANISM: Artificial Sequence
<220> FEATURE:
<223> OTHER INFORMATION: Primer No. 7

<400> SEQUENCE: 7

```
ctgatcttgt ccatctcgtg tgccacgggt ggca                                 34
```

<210> SEQ ID NO 8
<211> LENGTH: 802
<212> TYPE: DNA
<213> ORGANISM: Nannochloropsis oculata

<400> SEQUENCE: 8

```
ggcggtcttt tgtcctttcc tctatagccc gcccgtctag agggcacacg cgatgatctt      60
tatatctctt catgtgtctt tgttttaact aggatactgc cgggtgaatg cccatcggac     120
aagaggccaa actctatcta cacccttttg acttctgttg tggtcgtagt gtgtgcttgc     180
atgccctgaa agtccaggca tcccacttgt gctctaaccc cattcaaaac agcagaagtg     240
cttaattaag atatagattc atgatctcct gtccccctcct tcttaccttt tcacaaacct     300
cacacagaag tctccactct tcgcctctaa aacctctttt taaattatgg taagttcgtg     360
cggcagtggg ttttcggatc tatatttgtc aaggatccagt tcaaggtcag ggatgtagat    420
taagtacaga aggagaagca caagcgcgcc agttcgcccc tcacggcctg gagcagggca     480
tttaatccct ctatcttacc agaaccatac tatacaacca atcctgttgg catcgctctg     540
tctatttgtc gtgcgtgcat gtgtccatgg tgtggtgggg ggcaggggtt ttcggggttg     600
cggttgaagg caccttatca gaaagatgcc ctcagagata gaggtagccc cctccccccg     660
atcttcgacc agtcctgtca ggcgaacact ttcacccgtc gttcacctcg ttacacacaa     720
ggagtagacc tctgaagttc taattgtcat aaatgcccct cccccctccc tctttccctt     780
gatcctcccc tccgagcaga tt                                              802
```

<210> SEQ ID NO 9
<211> LENGTH: 643
<212> TYPE: DNA
<213> ORGANISM: Nannochloropsis oculata

<400> SEQUENCE: 9

```
gcttctgtgg aagagccagt ggtagtagca gtagcagcag cagtagcagc cgcagcactc      60
agtgttggcg cgagagattg tccatcccctt cttaacctac cggaagagaa ataaggcctt    120
tctcccgtag ctgtcttcgt ttgtttgtgc tgattgcttg atatgagagt gttgaattcc     180
tgcatcatgt ttttctctgt agtccttttcc taccccgtc attttcttttt ctccctggtt    240
cttctttttgt caccccttatt ttacataaaa ttttctttgt ttatagtgag aggaaggtag    300
agaggggaaa acaagaacaa cgaacgcaag cgtgtgaaag gagggcgagt agaagagaaa     360
cagatctgtt gagcattgag agtggagccg ggggaaaggc ttgtgtgttg tcttttgaaaa    420
agttgtttaa atcacgaatc cgttagttct catgtgtacc tctttcacta catgtgatgg     480
agaaaacaaa agtgtgagga ttaattgaag aaaaagaaga gttcgacacg tcaaaccgcc     540
caaaagacgt cacaaagaga acttgattct ctttgccgtg ttgatcctgt cttttccccc     600
agcttttctt gccacccgtg gcacacgaga tggacaagat cag                       643
```

<210> SEQ ID NO 10

```
<211> LENGTH: 47
<212> TYPE: DNA
<213> ORGANISM: Artificial Sequence
<220> FEATURE:
<223> OTHER INFORMATION: Primer No. 10

<400> SEQUENCE: 10
ggacaaaaga ccgccagctg tttcctgtgt gaaattgtta tccgctc          47

<210> SEQ ID NO 11
<211> LENGTH: 49
<212> TYPE: DNA
<213> ORGANISM: Artificial Sequence
<220> FEATURE:
<223> OTHER INFORMATION: Primer No. 11

<400> SEQUENCE: 11
gatggacaag atcagttaag ccagccccga cacccgccaa cacccgctg         49

<210> SEQ ID NO 12
<211> LENGTH: 35
<212> TYPE: DNA
<213> ORGANISM: Artificial Sequence
<220> FEATURE:
<223> OTHER INFORMATION: Primer No. 12

<400> SEQUENCE: 12
acacaggaaa cagcttagct atccatcttg tcctg                       35

<210> SEQ ID NO 13
<211> LENGTH: 35
<212> TYPE: DNA
<213> ORGANISM: Artificial Sequence
<220> FEATURE:
<223> OTHER INFORMATION: Primer No. 13

<400> SEQUENCE: 13
ggacaaaaga ccgccacctt aaatgcaatt ccttg                       35

<210> SEQ ID NO 14
<211> LENGTH: 35
<212> TYPE: DNA
<213> ORGANISM: Artificial Sequence
<220> FEATURE:
<223> OTHER INFORMATION: Primer No. 14

<400> SEQUENCE: 14
gatggacaag atcagagcag cccttcgaac tagac                       35

<210> SEQ ID NO 15
<211> LENGTH: 35
<212> TYPE: DNA
<213> ORGANISM: Artificial Sequence
<220> FEATURE:
<223> OTHER INFORMATION: Primer No. 15

<400> SEQUENCE: 15
tcggggctgg cttaaggcac atgtttatgc ctgtc                       35

<210> SEQ ID NO 16
<211> LENGTH: 5096
<212> TYPE: DNA
<213> ORGANISM: Nannochloropsis oculata

<400> SEQUENCE: 16
gatgagagga agaggggggc ggggcacaga agcagcatcg ggagcagtag caagaggctt    60
```

-continued

```
aggtagaggc atggaagata gatagaagaa ggagaaaagg agaggctgac ggcaaggaag      120
gaaggggccc agacaccaaa tgaatgaatt atcctgatca tgactccatt tcccggccct      180
cttcttccga cgggaagtgt ggtgacccac aggcatagag gacataggtg gagggaagga      240
gattgtgggg tttggttagc tgcgttattt ttatacatca aaacgcatgc acattgttca      300
gccatgcgct cggatgcgac caggcgagca gggcgggagg gataaaggtc tctttattga      360
aagagagata gttggtgagc ggaaatgatt tactggcgcg aaacgaaatg tgctgcggtg      420
tgacagtttt ggagcaaggg gggtacaatc cgtatccatc gatagaagaa aaaatataat      480
gcataatgtc tgtcatttct ttcgctcacg tttcatcccg tgggaggagg atgacgactg      540
aaactttctt ttgttcctta ttttcctttc catcagcagc tgggcgatct tctgtcatgg      600 cttttttcctc ttagcttctt tctctcttac attcacacat tcgcacaata tgctcgtgga      660
aagacgacac tgacaagcca tactgttttg ggccttgacg tggcgttctc tttcctgttt      720
ctttcatctc tagctggacc gttcggtgtg tggtgtggga gtgggtactg ttgttgttga      780
tgttgtagta gaaaaaatat acttcccaca atcgtatcat gtgcataacc cgaccgaaaa      840
ataaacgcat agtccccatt ttatcccatt ctcagcgtcc cttcgtggc cttctccctg      900 ttttaggact cttctcgggt cttgtcgtgg tgcttcttgt gcttcttgtg tttcttcttc      960
ttggacttct tcacctcttt ctcctctgac gtgtctgact ctgtgtcctc ttcctcctcc     1020
tgctcctctg catccttggc cgacgccatc accggggcag tcgccttgac agcggctcct     1080 ccctccccc caccaccgcc gccggttttg ttggccttgt agctatccat cttgtcctgg     1140
tacactgtct tctcctccac tgcaagcttc tgatactttt ccttctcctc ttcgctcagc     1200
tttttccagt cgttagctag cacccccatg agctccttca tcttggcctc tggctgggcc     1260
gcacgcagcg tcgggtgtg ctcacagaca taaaactggt acccgctctt gggccgtttc     1320
ggcaagtccg gatcccgctt cgccttgcgc ttcttcccat ttcccgctcc gttcgcctcc     1380
tccggggagg gctgtgcgtc gggcagcttc agcacagctt cgagggtagc cttgtcccca     1440
gcggccagct tggcaaagac tgcggcctgc tgggcggcaa agacttgttg tttctgaaag     1500
agcttcgcat agcacaacga gagcttctgg ggatccaaaa gagcgccttc tgccatggtg     1560
ctggtggtgt tgtgtgatct aggtgtgtta aagttttggg ccggaaaagc ggttgtgtgt     1620
caatcgtgcg cgaaggattt tgctgaaggg gggcaaataa gtgcttacct tgtcgcttgt     1680
ggggacgcca aacttggtgc cactgacgct ccccaaagtt gtggtgtctg tgtggtgttg     1740
tgtggtggtg gatgggctgg tatctttgag cgacactgta aagcaactac tccacaacag     1800
agagaacatc attgatcgtc atagatgatc tctatctcgt gcttcttgtt cgtcgaaacg     1860
caggcggctc ccatgcccaa agttgcttta cgactgcgcc catgtctcac cctctcgttt     1920
accttctcct tccttacaca gttacacaag tacaagagaa acaaaggca ttgcggacgc     1980 atgtcaccgt actacgaaga cgaagaggaa agggacgagg aagagcaaga ggttatgaag     2040
gacttccaga cgatggagga caatttgatg gtgctgattg atgcccgccc agcgatgctg     2100
gctaagaacg cggacggtaa ggtacgtgct aatgaggaga gactgcaggg cgaatgaggt     2160
ggattggaag cggcatcaat tgaacacagc ctgccggcta gggaatgtcg cgcttctcat     2220
cacaaggagg gtacgcgaaa ggggtggacc tggctcatgg gatctgttca tattacttgt     2280
gttcatgccg ctcgattttg catatgtata tcccaccccct tcccattttc tccctctttt     2340
ccttcctcta tctagtcccc gctaagaatt gcttttgaac tggcgcagtt cgtgctgcga     2400
```

```
cagaagatta tgatgagtcg tcgggactgg gtcggagttg tgcttttcgg ggtagataag      2460
gcagtggatg ataagtcgga ggaaaatggc ggccaagcag gaggttcgat gacattcggc      2520
gccagccaat tgcttgaggg ccatacgacc gagttgcaac ccttggggga accgaccgcc      2580
aaacgcatca agcaactgga gcggctgtgc aacccgacg tcgatgttgc caaggaattg       2640
catttaaggt ggacagactc ctcctctttt acctcttcat ccggcttacg ggacgggttc      2700
cgagcgtgtc tgcggatgct ggagacccgg tccaaaaagg aacgggacat tcggcgcatc     2760
tggcttctca ccaacgagga cgacccctcg agcccaaca acccaagcca agtaataaaa       2820
gatgcccaag agggaggggt ggatgtacgc ttgtggcatt ttcctcatcc cgacggccgg      2880
gatttcgacg agcgaaagct ttatgggccc gtgctctccg ccgcgagtaa gcagcccttc     2940
gaactagact acatcaaggc agacgaggaa gagaccgagt ccgagtcgaa gatggtaaat     3000
gtcgggagcg gggacatgac aactctgctg ggggcagcca agggtcgact atttaagaag     3060
cgtcgctacg cctgcaccat ctggcaagtt actgactcgc ctcccctctc catcaacgtt     3120
gccctttaca agaccatcca accctgtaaa aacccacgc ccgtgcagct ggccgcggct       3180
acaaatcgac ggctagttcc gagcaccaag tggctatgtg aggagctggt gcaatacatt     3240
gacttggagc tggaggcagc ttacggcctt gacttcgggt cctccaacac caccgtcccc     3300
ttcaaacgcc ctgagtttga atacaccctc cgcgctggtc ttagcgagcc cgggctctat     3360
ttgctgggat ttgtgccctc tgaggagctg gcatgggagc tgaacgtgac gagcagcacg     3420
acggtctacc cagaagagct ctcgctcaag ggttgcactc gtgccttcat ctccctgcgg     3480
gaggcgatgc tgaagcgtga gcggatggca gtggtccggt atcaggcgtc ggcaaagtca     3540
gagcctcgtc tagctgtgct acttgcttca ttggcaacca agggtttaga attggttgag     3600
ttgccttctc tgggcgatct gcgttctgtg gagagcccgc atctggactg tccccgccg     3660 ccgccggaga agaacagct ggaggcagct aggaaggtgg tggcgcgctt gactttaaag      3720
ccacagcagt actctgtggg cttcaataat ccggccttgg aaaagttta ctcgggtttg      3780 caggcgttgg cgctggagga ggcaaagacg gagtggaatg agataacgga tgacagcacc     3840
tggccctcgg acgagttgct tggccgagca agaagaagagt tggaggagct gtgggaactg    3900
tctcctgatc caagaaaggg tgtgcagagg gggaggggga ggaagcggaa ggcagatgca     3960
gtgacgaaaa ctgttaaggg taagctggtc gctgagaagg tcagcaaggc tgaagacgag     4020
gatgatgaga agataggagg cggtggcgat agatcggtga aggacctttc gatgggaaag     4080
ctggccaaac tgacggttcc tcaactgaag gagatctgtc gtgcacgtgg gttgcccgtg     4140
tcaggcaaga agggagacat catcgatcgt ttacagatgg acctcgagac cgatgatgac     4200
ttgtgatgag acgaggcaag tgtttctggt agaggaatat tttaagaaga gtatgtgaat     4260
atcatgtgga tatatggacg atcagaacaa aactaaagag ttgtgcaata gagagacgag     4320
ggggaaccgg agaataagga cccccgcctt agcgcagcct ttcaaaccca ggacagcgac    4380
agtcacataa aagaaacata acatataaat aaatcctcat aacatgccat tgggggcag     4440 tgattgcgct tgtttgccct gtgacgccat tacctcccgc ttactgacgg tccggtcgag    4500
gacaggcata aacatgtgcc cgagccgcac aatcctcgtg accattaagc agaagaactg    4560
agcgccttat ccacgagggt gcgatacttt ggatcggact gctccgacca gcgccattaa    4620 aagcccccaga gggtacactc caaagaaaag aagacatacc atacgccatc gtcgcttttt  4680
ccctcgccgg cgtcctccac cattggtcgg gaggtgcgtt gaagcatttt acttcacgtt     4740
gtggggtggc ccacatgtcc gagctctggc acgaggagga agcgcggtaa agacacctgt    4800
```

```
gacctccctc ccgcatctca tcatcataat acggccctgg cccagttgcc tttctgcttg    4860
tcttgacggg gcgataagaa agcaatggga gcggcaacca ttgtatactt ccacgcttg     4920 aaagctactc atttaacatg atggcatggc agtggtgcaa gtgctggtca ggcgctcacc    4980
gtcgtgcaag caaccccct tcttcaagtg gccgtatggg gcgaggcggc aagtaccacc     5040
acctcgcccc agccctcctc cacttgaata tccgcctcac aaactcaccc tgacaa        5096
```

<210> SEQ ID NO 17
<211> LENGTH: 1531
<212> TYPE: DNA
<213> ORGANISM: Nannochloropsis oculata

<400> SEQUENCE: 17

```
tagctatcca tcttgtcctg gtacactgtc ttctcctcca ctgcaagctt ctgatacttt      60
tccttctcct cttcgctcag cttttttccag tcgttagcta gcaccccccat gagctccttc   120 atcttggcct ctggctgggc cgcacgcagc gtcggggtgt gctcacagac ataaaactgg     180
tacccgctct tgggccgttt cggcaagtcc ggatcccgct tcgccttgcg cttcttccca    240
tttcccgctc cgttcgcctc ctccggggag ggctgtgcgt cgggcagctt cagcacagct   300
tcgagggtag ccttgtcccc agcggccagc ttggcaaaga ctgcggcctg ctgggcggca    360
aagacttgtt gtttctgaaa gagcttcgca tagcacaacg agagcttctg gggatccaaa    420
agagcgcctt ctgccatggt gctggtggtg ttgtgtgatc taggtgtgtt aaagttttgg    480
gccggaaaag cggttgtgtg tcaatcgtgc gcgaaggatt ttgctgaagg ggggcaaata    540
agtgcttacc ttgtcgcttg tggggacgcc aaacttggtg ccactgacgc tccccaaagt    600
tgtggtgtct gtgtggtgtt gtgtggtggt ggatgggctg gtatctttga gcgacactgt    660
aaagcaacta ctccacaaca gagagaacat cattgatcgt catagatgat ctctatctcg    720
tgcttcttgt tcgtcgaaac gcaggcggct cccatgccca agttgctttt acgactgcgc    780
ccatgtctca ccctctcgtt taccttctcc ttccttacac agttacacaa gtacaagaga    840
aaacaaaggc attgcggacg catgtcaccg tactacgaag acgaagagga aagggacgag    900
gaagagcaag aggttatgaa ggacttccag acgatggagg acaatttgat ggtgctgatt    960
gatgcccgcc cagcgatgct ggctaagaac gcggacggta aggtacgtgc taatgaggag   1020
agactgcagg gcgaatgagg tggattggaa gcggcatcaa ttgaacacag cctgccggct    1080
agggaatgtc gcgcttctca tcacaaggag ggtacgcgaa aggggtggac ctggctcatg    1140
ggatctgttc atattacttg tgttcatgcc gctcgatttt gcatatgtat atcccacccc    1200
ttcccatttt ctccctcttt tccttcctct atctagtccc cgctaagaat tgcttttgaa    1260
ctggcgcagt tcgtgctgcg acagaagatt atgatgagtc gtcgggactg gtcggagtt    1320 gtgcttttcg gggtagataa ggcagtggat gataagtcgg aggaaaatgg cggccaagca    1380
ggaggttcga tgacattcgg cgccagccaa ttgcttgagg gccatacgac cgagttgcaa    1440
ccccttgggg gaaccgaccgc caaacgcatc aagcaactgg agcggctgtg ccaacccgac    1500
gtcgatgttg ccaaggaatt gcatttaagg t                                   1531
```

<210> SEQ ID NO 18
<211> LENGTH: 1591
<212> TYPE: DNA
<213> ORGANISM: Nannochloropsis oculata

<400> SEQUENCE: 18

-continued

| | |
|---|---:|
| agcagccctt cgaactagac tacatcaagg cagacgagga agagaccgag tccgagtcga | 60 |
| agatggtaaa tgtcgggagc ggggacatga caactctgct gggggcagcc aagggtcgac | 120 |
| tatttaagaa gcgtcgctac gcctgcacca tctggcaagt tactgactcg cctcccctct | 180 |
| ccatcaacgt tgcccttttac aagaccatcc aaccctgtaa aaaacccacg cccgtgcagc | 240 |
| tggccgcggc tacaaatcga cggctagttc cgagcaccaa gtggctatgt gaggagctgg | 300 |
| tgcaatacat tgacttggag ctggaggcag cttacggcct tgacttcggg tcctccaaca | 360 |
| ccaccgtccc cttcaaacgc cctgagtttg aatacaccct ccgcgctggt cttagcgagc | 420 |
| ccgggctcta tttgctggga tttgtgccct ctgaggagct ggcatgggag ctgaacgtga | 480 |
| cgagcagcac gacggtctac ccagaagagc tctcgctcaa gggttgcact cgtgccttca | 540 |
| tctccctgcg ggaggcgatg ctgaagcgtg agcggatggc agtggtccgg tatcaggcgt | 600 |
| cggcaaagtc agagcctcgt ctagctgtgc tacttgcttc attggcaacc aagggtttag | 660 |
| aattggttga gttgccttc ttgggcgatc tgcgttctgt ggagagcccg catctggact | 720 |
| gtcccccgcc gccgccggag aaagaacagc tggaggcagc taggaaggtg gtggcgcgct | 780 |
| tgactttaaa gccacagcag tactctgtgg gcttcaataa tccggccttg gaaaagtttt | 840 |
| actcgggttt gcaggcgttg gcgctggagg aggcaaagac ggagtggaat gagataacgg | 900 |
| atgacagcac ctggccctcg gacgagttgc ttggccgagc agaagaagag ttggaggagc | 960 |
| tgtgggaact gtctcctgat ccaagaaagg gtgtgcagag ggggaggggg aggaagcgga | 1020 |
| aggcagatgc agtgacgaaa actgttaagg gtaagctggt cgctgagaag gtcagcaagg | 1080 |
| ctgaagacga ggatgatgag aagataggag gcggtggcga tagatcggtg aaggaccttt | 1140 |
| cgatgggaaa gctggccaaa ctgacggttc ctcaactgaa ggagatctgt cgtgcacgtg | 1200 |
| ggttgcccgt gtcaggcaag aagggagaca tcatcgatcg tttacagatg gacctcgaga | 1260 |
| ccgatgatga cttgtgatga gacgaggcaa gtgtttctgg tagaggaata ttttaagaag | 1320 |
| agtatgtgaa tatcatgtgg atatatgac gatcagaaca aaactaaaga gttgtgcaat | 1380 |
| agagagacga gggggaaccg gagaataagg accccgcct tagcgcagcc tttcaaaccc | 1440 |
| aggacagcga cagtcacata aaagaaacat aacatataaa taaatcctca taacatgcca | 1500 |
| tttgggggca gtgattgcgc ttgtttgccc tgtgacgcca ttacctcccg cttactgacg | 1560 |
| gtccggtcga ggacaggcat aaacatgtgc c | 1591 |

<210> SEQ ID NO 19
<211> LENGTH: 32
<212> TYPE: DNA
<213> ORGANISM: Artificial Sequence
<220> FEATURE:
<223> OTHER INFORMATION: Primer No. 19

<400> SEQUENCE: 19

| | |
|---|---:|
| agctgtttcc tgtgtgaaat tgttatccgc tc | 32 |

<210> SEQ ID NO 20
<211> LENGTH: 34
<212> TYPE: DNA
<213> ORGANISM: Artificial Sequence
<220> FEATURE:
<223> OTHER INFORMATION: Primer No. 20

<400> SEQUENCE: 20

| | |
|---|---:|
| ttaagccagc cccgacaccc gccaacaccc gctg | 34 |

```
<210> SEQ ID NO 21
<211> LENGTH: 30
<212> TYPE: DNA
<213> ORGANISM: Artificial Sequence
<220> FEATURE:
<223> OTHER INFORMATION: Primer No. 21

<400> SEQUENCE: 21
tagctatcca tcttgtcctg gtacactgtc                                     30

<210> SEQ ID NO 22
<211> LENGTH: 31
<212> TYPE: DNA
<213> ORGANISM: Artificial Sequence
<220> FEATURE:
<223> OTHER INFORMATION: Primer No. 22

<400> SEQUENCE: 22
ggcacatgtt tatgcctgtc ctcgaccgga c                                   31

<210> SEQ ID NO 23
<211> LENGTH: 20
<212> TYPE: DNA
<213> ORGANISM: Artificial Sequence
<220> FEATURE:
<223> OTHER INFORMATION: Primer No. 23

<400> SEQUENCE: 23
tagctatcca tcttgtcctg                                                20

<210> SEQ ID NO 24
<211> LENGTH: 20
<212> TYPE: DNA
<213> ORGANISM: Artificial Sequence
<220> FEATURE:
<223> OTHER INFORMATION: Primer No. 24

<400> SEQUENCE: 24
gtcttctttt ctttggagtg                                                20

<210> SEQ ID NO 25
<211> LENGTH: 822
<212> TYPE: DNA
<213> ORGANISM: Artificial Sequence
<220> FEATURE:
<223> OTHER INFORMATION: Paromomycin resistance gene

<400> SEQUENCE: 25
atggtcgaga ttcgaagcat ggacgatgcg ttgcgtgcac tgcggggtcg gtatcccggt     60
tgtgagtggg ttgttgtgga ggatggggcc tcggggctg  gtgtttatcg gcttcgggt    120 ggtgggcggg agttgtttgt caaggtggca gctctggggg ccggggtggg cttgttgggt   180
gaggctgaac ggctggtgtg gttggcggag gtggggattc ccgtacctcg tgttgtggag   240
ggtggtgggg acgagagggt cgcctggttg gtcaccgaag cggttccggg gcgtccggcc   300
agtgcgcggt ggccgcggga gcagcggctg gacgtggcgg tggcgctcgc ggggctcgct   360
cgttcgctgc acgcgctgga ctgggagcgg tgtccgttcg atcgcagtct cgcggtgacg   420
gtgccgcagg cggcccgtgc tgtcgctgaa gggagcgtcg acttggagga tctggacgag   480
gagcggaagg ggtggtcggg ggagcggctt ctcgccgagc tggagcggac tcggcctgcg   540
gacgaggatc tggcggtttg ccacggtgac ctgtgcccgg acaacgtgct gctcgaccct   600
cgtacctgcg aggtgaccgg gctgatcgac gtggggcggg tcggccgtgc ggaccggcac   660
```

```
tccgatctcg cgctggtgct gcgcgagctg gcccacgagg aggacccgtg gttcgggccg      720
gagtgttccg cggcgttcct gcgggagtac gggcgcgggt gggatgggc ggtatcggag       780 gaaaagctgg cgttttaccg gctgttggac gagttcttct ga                        822
```

```
<210> SEQ ID NO 26
<211> LENGTH: 45
<212> TYPE: DNA
<213> ORGANISM: Artificial Sequence
<220> FEATURE:
<223> OTHER INFORMATION: Primer No. 26

<400> SEQUENCE: 26
ccctccgagc agattatggt cgagattcga agcatggacg atgcg                      45

<210> SEQ ID NO 27
<211> LENGTH: 46
<212> TYPE: DNA
<213> ORGANISM: Artificial Sequence
<220> FEATURE:
<223> OTHER INFORMATION: Primer No. 27

<400> SEQUENCE: 27
ctcttccaca gaagctcaga agaactcgtc caacagccgg taaaac                     46

<210> SEQ ID NO 28
<211> LENGTH: 35
<212> TYPE: DNA
<213> ORGANISM: Artificial Sequence
<220> FEATURE:
<223> OTHER INFORMATION: Primer No. 28

<400> SEQUENCE: 28
acacaggaaa cagctgaatg catgccggcc gagaa                                 35

<210> SEQ ID NO 29
<211> LENGTH: 35
<212> TYPE: DNA
<213> ORGANISM: Artificial Sequence
<220> FEATURE:
<223> OTHER INFORMATION: Primer No. 29

<400> SEQUENCE: 29
ggacaaaaga ccgccggagc aggacagaat gggct                                 35

<210> SEQ ID NO 30
<211> LENGTH: 35
<212> TYPE: DNA
<213> ORGANISM: Artificial Sequence
<220> FEATURE:
<223> OTHER INFORMATION: Primer No. 30

<400> SEQUENCE: 30
gatggacaag atcagtgcgg ggatgccaaa gatct                                 35

<210> SEQ ID NO 31
<211> LENGTH: 35
<212> TYPE: DNA
<213> ORGANISM: Artificial Sequence
<220> FEATURE:
<223> OTHER INFORMATION: Primer No. 31

<400> SEQUENCE: 31
tcggggctgg cttaagtttc aggcggtgga aagcg                                 35
```

<210> SEQ ID NO 32
<211> LENGTH: 3400
<212> TYPE: DNA
<213> ORGANISM: Nannochloropsis oculata

<400> SEQUENCE: 32

```
ccactcccca gccggactcc gcatcaagcc caccatgtac ccccagctta gcccacatgc      60
ccaagctatc tacaagaagc tgacggcctt tgtggacgag gaatgcatgc cggccgagaa     120
agtgtttgag gagcagcatg cagcattgtc ttcccggtgg atggtccccg cggtcgtcga     180
gaccctcaag gccaaagcca agaggttagg cctatggaac ctctttatga tggaagagca     240
cgtgcatcac tccgggctga aaatgacgga gtacgctgtt atgagtgagg tcatgggtcg     300
gtcctttctg gcgcccgagg catgtaattg caatgcgcca gacacgggta acatggaagt     360
gttggcaaag tatggcaacg ccgcgcaaca agcacggtgg ctcactccct taatggcagg     420
caccatccgc tctacctttc tcatgactga acccgccgtc gcctcgtcgg atgcgaccaa     480
tatttgcacg aacttctgta gggaaggcga tgagtatgtg gtgaatggcc gcaagtggtg     540
gagctccggc gccatggacc cccgttgcca agtcgcgctt gtgatgggca aggtagaagg     600
cgccgccacc aacgctgccc gtcggcatca gcagcattcc atcttgattg tacccatgga     660
cacacccggg ctcaaggtct tgcgccctct gaccgttttt gggttcgacg atgcccccca     720
cggtcacgcc gaggtggaac ttgtgaatgt gcgtgtgccc gtcagcaacc tggtcctggg     780
agaaggggac ggcttcaaaa ttgcacaagg ccgcttaggc ccggggcgga tccaccattg     840
tatgcgagca attgggctgt cggagcgcgt gttggcgttg gcgattaagc gagccatgac     900
gcgcaaggct tttggacagg agctcgcgcg acaaggcacc gtgcaacggg acttggcgca     960
gtgccggatg gagttagacc aggcacgatt gttggtgttg cacgctgcct ggcggatgga    1020
tacgaatggc ggggccaaag gtgcacaaca ggagattgcg atgatcaagg ttgtagcgcc    1080
gaatatgggc caacgggtgg tggacactgc cattcagatt catggtggta tgggcgtgtg    1140
tcaagacact attctggcac gggcatttgc gtacatgcgc tcactgcgta ttgcagacgg    1200
gcccgatgtg gtgcattcac gaacggtggc gcgccatgag ttgaagcgga tgatagatgg    1260
caagacacag ctatctgcgg acgcgtggta taggagcacc catggcgtca ccagtgtgaa    1320
cagcaggctt tgattaggtt gaaacaagaa cacgaacaaa atcacgtaaa ttttttgttca   1380 attattaagg tagcttctgt acattcaaaa ttttgatata tttcttatgc tttgtaccct    1440
atccctaata attcatagct attttgacaa caatctagcc ttgacaatat gcttccaaac    1500
acgaagtaca ctgggatgtg gtcgcccaaa agcccattct gtcctgctcc gacaagctag    1560
cggcaaacaa acatgccaaa cactttctga aatcagaagc tttaagctgg tcttgtccgt    1620
tcctgacaat atcgtcgacg tctgcagctt gcagagggtc tgcggggatg ccaaagatct    1680
ggtttagccc taaggcactc cgaagtgccg taaaaccact cttgccactg gaaaccaccc    1740
ggttgggtac ataaacaatg gcagtaacgt tgggctcacg gcacccgaaa aaactgacctt   1800 gcgttgtgtg ccgtggattc gtaaacccccg gtttgggat atccgctggc aaggtatgct    1860
cctcactgag ctccgagagg cggaacaagt cgtttagcac tggatcggct gtaggccagc    1920
acgcattgtc cagcaaaggc tcacatgttg aacagcattt gttgttcagg ccgccgtcag    1980
cctcgtaata taaatttgag gcgcaagagg ccgacgcgcc cggcgccgaa tcggtggcgc    2040
acgaggcctc cggtcccgtc gaaatgggag catcgaaggt cttcccacct ttactcccac    2100
tcgaatcgat gacgatcaca acgtccgcct gtcgcgtagg agttacaaag ggccagaccg    2160
```

| | |
|---|---:|
| ggttgttgta cgtagcggcg ccgtccagga cctttgtttc ggcacttgta aacaggtccg | 2220 |
| gcatgccttc tgcggccgct gcctgactac tcggacccc atgaccaaca aacgggttgt | 2280 |
| ttatgagcac cggctggcat gcgcttccgg cttcgccgca tacaactgat tgaagcgtcc | 2340 |
| cccccgata ttcttgagcc aaagggaaaa tccagccgga cacacccatg agccatgaaa | 2400 |
| cctggtcaat ttgcgttgta cagcgcttgt tcgggtcctc agcatccgtc ccaagcaatg | 2460 |
| ctgtggggta ggagacatgc acttcacctt tgtgcacgcc cacgtcaaac ggcgagactt | 2520 |
| cccaaaatcg aaaagcactt ccttgggcgt tctgaagaag catcaacggc aaaggtgcgt | 2580 |
| tatgatttcc gaccagccca tccaaaagca gacctgacat tgtaagcccc atccctccat | 2640 |
| cctgaaacgg cgcaccaagc atctggtaag ccaaggcgcg tccccaatac tcactcaaag | 2700 |
| cagggcttcc ggcttgacta gctttggtcg ctgggctctg aaacttgagc tcactctgac | 2760 |
| ataggatgtt tgcggtcgtt gttgcagcag aatcctggaa agcaaagggc gccacaggca | 2820 |
| aggatactcc accattaatg ccaaaattgg tcaaaatgtc attggctcga aaggtcccat | 2880 |
| caaacacagc tttggtcaag tccggcatgc gcgcactgat aaaggttgcc ggatcaatta | 2940 |
| aaccctcctt gcccagacta gccccataca aaccacccaa caaccaactt ccacccgagg | 3000 |
| acccggccat ccatgtcgca aggtccaata cgcctgcctg cgccaagttg gaagtcacac | 3060 |
| cggcagcatt gaaagagag cgcttttccac cgcctgaaac ggcaatcgcc accttcaaat | 3120 |
| ccgtgcgtgc cgagggtcc agcgcaaaga gattctgctc aataaaagaa gcaagcttgg | 3180 |
| ggcctgtctt gagcagacgc tgcgcaaccc attccttttc ctcagggtgc agttcgtcaa | 3240 |
| aggtggcatt gtctaggact cgagaagccg atgaagatcg cttgggaaag acggggcagt | 3300 |
| cggcgctaga ggccgagaga agaggtacag cagaatttat tctcgagagt ccttgtgctg | 3360 |
| tgctgcctgg taaacacgtc atgcttgtgg ctggagcctg | 3400 |

<210> SEQ ID NO 33
<211> LENGTH: 1450
<212> TYPE: DNA
<213> ORGANISM: Nannochloropsis oculata

<400> SEQUENCE: 33

| | |
|---|---:|
| gaatgcatgc cggccgagaa agtgtttgag gagcagcatg cagcattgtc ttcccggtgg | 60 |
| atggtccccg cggtcgtcga gaccctcaag gccaaagcca agaggttagg cctatggaac | 120 |
| ctctttatga tggaagagca cgtgcatcac tccgggctga aaatgacgga gtacgctgtt | 180 |
| atgagtgagg tcatgggtcg gtcctttctg gcgcccgagg catgtaattg caatgcgcca | 240 |
| gacacgggta acatggaagt gttggcaaag tatggcaacg ccgcgcaaca agcacggtgg | 300 |
| ctcactccct taatgcagg caccatccgc tctaccttc tcatgactga acccgccgtc | 360 |
| gcctcgtcgg atgcgaccaa tatttgcacg aacttctgta gggaaggcga tgagtatgtg | 420 |
| gtgaatggcc gcaagtggtg gagctccggc gccatggacc ccgttgcca agtcgcgctt | 480 |
| gtgatgggca aggtagaagg cgccgccacc aacgctgccc gtcggcatca gcagcattcc | 540 |
| atcttgattg tacccatgga cacacccggg ctcaaggtct tgcgccctct gaccgttttt | 600 |
| gggttcgacg atgcccccca cggtcacgcc gaggtggaac ttgtgaatgt gcgtgtgccc | 660 |
| gtcagcaacc tggtcctggg agaaggggac ggcttcaaaa ttgcacaagg ccgcttaggc | 720 |
| ccggggcgga tccaccattg tatgcgagca attgggctgt cggagcgcgt gttggcgttg | 780 |
| gcgattaagc gagccatgac gcgcaaggct tttggacagg agctcgcgcg acaaggcacc | 840 |
| gtgcaacggg acttggcgca gtgccggatg gagttagacc aggcacgatt gttggtgttg | 900 |

```
cacgctgcct ggcggatgga tacgaatggc ggggccaaag gtgcacaaca ggagattgcg      960
atgatcaagg ttgtagcgcc gaatatgggc caacgggtgg tggacactgc cattcagatt     1020
catggtggta tgggcgtgtg tcaagacact attctggcac gggcatttgc gtacatgcgc     1080
tcactgcgta ttgcagacgg gcccgatgtg gtgcattcac gaacggtggc gcgccatgag     1140
ttgaagcgga tgatagatgg caagacacag ctatctgcgg acgcgtggta taggagcacc     1200
catggcgtca ccagtgtgaa cagcaggctt tgattaggtt gaaacaagaa cacgaacaaa     1260
atcacgtaaa ttttttgttca attattaagg tagcttctgt acattcaaaa ttttgatata    1320
tttcttatgc tttgtaccct atccctaata attcatagct attttgacaa caatctagcc     1380
ttgacaatat gcttccaaac acgaagtaca ctgggatgtg gtcgcccaaa agcccattct     1440
gtcctgctcc                                                           1450

<210> SEQ ID NO 34
<211> LENGTH: 1440
<212> TYPE: DNA
<213> ORGANISM: Nannochloropsis oculata

<400> SEQUENCE: 34
tgcggggatg ccaaagatct ggtttagccc taaggcactc cgaagtgccg taaaaccact       60
cttgccactg gaaccacccc ggttgggtac ataaacaatg gcagtaacgt tgggctcacg      120
gcacccgaaa aaactgactt gcgttgtgtg ccgtggattc gtaaaccccg gtttggggat      180
atccgctggc aaggtatgct cctcactgag ctccgagagg cggaacaagt cgtttagcac      240
tggatcggct gtaggccagc acgcattgtc cagcaaaggc tcacatgttg aacagcattt      300
gttgttcagg ccgccgtcag cctcgtaata taaatttgag gcgcaagagg ccgacgcgcc      360
cggcgccgaa tcggtggcgc acgaggcctc cggtcccgtc gaaatgggag catcgaaggt      420
cttcccacct ttactcccac tcgaatcgat gacgatcaca acgtccgcct gtcgcgtagg      480
agttacaaag ggccagaccg ggttgttgta cgtagcggcg ccgtccagga cctttgtttc      540
ggcacttgta acaggtccgg gcatgccttc tgcggccgct gcctgactac tcggaccccc      600
atgaccaaca aacgggttgt ttatgagcac cggctggcat gcgcttccgg cttcgccgca      660
tacaactgat tgaagcgtcc ccccccgata ttcttgagcc aaagggaaaa tccagccgga      720
cacacccatg agccatgaaa cctggtcaat ttgcgttgta cagcgcttgt tcgggtcctc      780
agcatccgtc ccaagcaatg ctgtggggta ggagacatgc acttcacctt tgtgcacgcc      840
cacgtcaaac ggcgagactt cccaaaatcg aaaagcactt ccttgggcgt tctgaagaag      900
catcaacggc aaaggtgcgt tatgatttcc gaccagccca tccaaaagca gacctgacat      960
tgtaagcccc atccctccat cctgaaacgg cgcaccaagc atctggtaag ccaaggcgcg     1020
tccccaatac tcactcaaag cagggcttcc ggcttgacta gctttggtcg ctgggctctg     1080
aaacttgagc tcactctgac ataggatgtt tgcggtcgtt gttgcagcag aatcctggaa     1140
agcaaagggc gccacaggca aggatactcc accattaatg ccaaaattgg tcaaaatgtc     1200
attggctcga aggtcccat caaacacagc tttggtcaag tccggcatgc gcgcactgat      1260
aaaggttgcc ggatcaatta aaccctcctt gcccagacta gccccataca aaccacccaa     1320
caaccaactt ccaccgagg acccggccat ccatgtcgca aggtccaata cgcctgcctg      1380
cgccaagttg gaagtcacac cggcagcatt gaaaagagag cgctttccac cgcctgaaac     1440

<210> SEQ ID NO 35
```

```
<211> LENGTH: 35
<212> TYPE: DNA
<213> ORGANISM: Artificial Sequence
<220> FEATURE:
<223> OTHER INFORMATION: Primer No. 35

<400> SEQUENCE: 35
acacaggaaa cagctaactc ggcgcaccca aaaag                        35

<210> SEQ ID NO 36
<211> LENGTH: 35
<212> TYPE: DNA
<213> ORGANISM: Artificial Sequence
<220> FEATURE:
<223> OTHER INFORMATION: Primer No. 36

<400> SEQUENCE: 36
ggacaaaaga ccgccacccc accaacgtcc ccttt                        35

<210> SEQ ID NO 37
<211> LENGTH: 35
<212> TYPE: DNA
<213> ORGANISM: Artificial Sequence
<220> FEATURE:
<223> OTHER INFORMATION: Primer No. 37

<400> SEQUENCE: 37
gatggacaag atcaggacgg gcatgattgt gatgg                        35

<210> SEQ ID NO 38
<211> LENGTH: 35
<212> TYPE: DNA
<213> ORGANISM: Artificial Sequence
<220> FEATURE:
<223> OTHER INFORMATION: Primer No. 38

<400> SEQUENCE: 38
tcggggctgg cttaatgtgg cagcactgtg tctta                        35

<210> SEQ ID NO 39
<211> LENGTH: 3600
<212> TYPE: DNA
<213> ORGANISM: Nannochloropsis oculata

<400> SEQUENCE: 39
accgacccat ggccttctcg ttcaccaagt ccgtcgtttg actacttaac atcgatgaaa      60
tcaatgtctg caacctcata tgctcagggg aagtggcgtg gcgttttccc aactcggcgc     120
acccaaaaag gtccacaggt gcagcagggc ctgcttcgcg cattttgcgg atgtgttcta     180
gttgttgctg ccagagggggg tgaggggaaa aggggggcga tgcagctttt ttgggtttag     240
gtactgcttt tggcttgatg gtccttgccg gtgcagcggc ggcgatactg ctcgtggata     300
tgttcttggt cttctttctg ggagcgattt ctgcaccagt ggactttttcc ttggcagcga     360
tcgcgggagg agtgacgggg tctgctgcag caatctgcac cgtgccgtct tcgttttcag     420
cccctgctgc ccgtgtgtgg cctctcagtg acagccggct ctcctgttga gagaaggtgt     480
ggtccactga agaaaaagaa aaggaaacag gagcccgcca cagtcccgat ccccggccac     540
caatggccga aaacgccaga ctgtgtgtgc tggtgttggg ttgggcccga tcggatgaga     600
cgaagaccaa agcagtcaga atgtagtata gataagaggg acgcacctat gcctgccgta     660
gaccacaatg caactcaacg atatgaccat atatgcgagt gtagtggcaa agagtgaacc     720
acgtgtgccg ctgcttggca ttggatgctc gagcggctgg ggctagagga gagttttgtg     780
```

```
ccacgacgtg atggggacca aagctgcggg ttttttgctg tcacaactcg atccttgaat    840
cattatgaga tggaaaaata tgcttaaaag gtactggtgc aatgggtaat gttgattcgg    900
gcgcaaggga caaagcccct gcacagatgc ttgaccctga ttcagggcca aggaactaac    960
gcccagtgct gatggcaacg ttttctgtg cgtaatgttg acattcttca cagcgtgatg   1020
ccacctcgca aaccatctg ctcaatgttt tgtccgctcc acacactggc attgatagga    1080
aaacattctc tcacgaagct accgccctc tttccccctc attttctcc gcggcctagc    1140 ctttacaaag cacctcaata catcaacgat gctgcggcga ctcttcctgc gctcgtccac    1200
ctctctctct cgcaccatcg ccaccatcac gcccggcttg tcccgtgccc ttgccactct    1260
ttctgttggc gcgcccgacc tccctcgtgc ctcgagcacc aacacgaagc ggcggttcga    1320
atggcaagac cccctgatgc tgcgggcgca attgacggag gaagagggca tgatccaaga    1380
catgacccgc gcctactgca agaaagcct gcaatcccgc atcctccaag cgaaccgcca    1440
cgaggagttt gaccggaaga tcctgacgga aatgggcgag ttgggcttgc tagggccgac    1500
cttaaaaggg tacggatgcc cgggagtggg atatgtggca tacggcctga ttgcccatga    1560
ggtggaagcg gtggatagtg cctatcgctc cgcgatgagc gtgcagtctt ctttggtcat    1620
gcatcctatt tatacgttcg gcacggagaa gcagaaggag acgtatttgc cggggttggc    1680 aaagggggacg ttggtggggt gtttcgggtt gacggagccg aatcatggtt cggacccggg    1740
gggaatggag acacgtgccc gccggcagaa ggacgggagt tcgtgttga gtggcagtaa    1800 aaactggatc accaactcac ccatcgcgga cgtgtttgtg gtatgggcga aggatgacga    1860
gggtgctatc cgggggttcg tcttggagaa ggggatggcc gggttaacag cgcctaaaat    1920
cgagggtaag ttctcgttgc gtgcgtcggc gacgggcatg attgtgatgg acgacgtaaa    1980
agtcccaggg gagaacttat tgccgaaagc caaggggtta ggagggcctt tctcgtgctt    2040
gaatagtgcg cggtacggca tctcgtgggg caccatgggg gcggctgggt tttgcatggc    2100
tactgcccgg gagtacgtgc tggacaggat gcagtttggg gcgcctttgg caagcaatca    2160
gctgatacaa aagaaactcg cagacatggg gactgagatt gcgcttggtc tccaggcgtc    2220
gttgagggta gggaggttac tggatcagaa agaggccgtg ccggagatga tctcgatggt    2280
aaagaggaat aattgtggga aggcgttgga ggtggtgagg gttgcaaggg atatgttggg    2340
agggaatgga atctcggacg aatatcatgt gattcgacat gtgatgaatt tggaggcggt    2400
taacacctat gaagggactc atgatgtgca tgcgttgata ctggggagag cgataacggg    2460
catcccggcg ttcgtgccgc ggaatagcac atttcagtaa gacagcagag gaagaggaaa    2520
acatgagaaa ggaagggagg gtgtgagatc gggagagaga gaggaggcat tgaagatgta    2580
aatatcatat agcataggcc cgggcgggca gttgtgcatt tgtaccgcgt cggatagctt    2640
aggaagttgg cggaagggat gggggcagag gagaagggta cgaggaaaga agtgaaagtt    2700
accaaaatcc gctgggcagg tgtgagttgt gtgtaagaaa ggaagcggg atggaaggaa    2760 gaaagattgt gaatagctat tccgtgctca caattttcta tgaaacatgt gcactttggc    2820
gagtagaaga gatgaaaaat taaacaaaag gtaaagctga tgtacaacca aaggatgagt    2880
atgaatgctt acggtacttt aatatctgtc gaggccgagg cctccgaggc caatttccac    2940
ttccacaaaa tgaaactctc atacaagcac tcgaccaaaa tctatgggac acatgtgggc    3000
ttgtaatgct cgcaccgcat gtggcctagg gtttgtgctc ctggctattg tatcaaaacg    3060
cttaattctc ccccgctcaa ttttttgcagg ctactggcac aaatcaagca gcctgcaagc    3120
```

```
acctggagat ggacatccgc cccgcgttga ggccgttacg cgtcgaacgg tcggcgggac    3180 aattttttgcc tatgggcgtc cattcctgat ataaagtatg acgactagtc gcccgcgaga    3240
tggtccgttg tcacccgatt tcttttgctc atgatttgac gaaggagccg atagaaacat    3300
aaaaatgtct tgttcttccg aagggggccc tttctttcat acaactacgg catattattg    3360
ccagtccgga atgctcgcca cgcatggtct gcgccgggcc catgagacat cacttctcag    3420
ccgcccggcg gtccccctg gagttgcgat gaacacccag cgagcatacg ttatataggc     3480
taagacacag tgctgccaca tacgcaggag caacctggac cactgagctt gtacttttgg    3540
ccagtcgctc catggcttgc ctgctgtgta aatgtagcat cgcgccggcc atgggcgcca    3600
```

<210> SEQ ID NO 40
<211> LENGTH: 1590
<212> TYPE: DNA
<213> ORGANISM: Nannochloropsis oculata

<400> SEQUENCE: 40

```
aactcggcgc acccaaaaag gtccacaggt gcagcagggc ctgcttcgcg cattttgcgg      60
atgtgttcta gttgttgctg ccagagggg tgagggaaa aggggggcga tgcagctttt      120
ttgggtttag gtactgcttt tggcttgatg gtccttgccg gtgcagcggc ggcgatactg     180
ctcgtggata tgttcttggt cttctttctg ggagcgattt ctgcaccagt ggacttttcc     240
ttggcagcga tcgcggagg agtgacgggg tctgctgcag caatctgcac cgtgccgtct     300
tcgttttcag cccctgctgc ccgtgtgtgg cctctcagtg acagccggct ctcctgttga     360
gagaaggtgt ggtccactga agaaaaagaa aaggaaacag gagcccgcca cagtcccgat     420
ccccggccac caatggccga aaacgccaga ctgtgtgtgc tggtgttggg ttgggcccga     480
tcggatgaga cgaagaccaa agcagtcaga atgtagtata gataagaggg acgcaccat     540 gcctgccgta gaccacaatg caactcaacg atatgaccat atatgcgagt gtagtggcaa     600
agagtgaacc acgtgtgccg ctgcttggca ttggatgctc gagcggctgg ggctagagga     660
gagttttgtg ccacgacgtg atggggacca agctgcgggg tttttgctg tcacaactcg     720 atccttgaat cattatgaga tggaaaaata tgcttaaaag gtactggtgc aatgggtaat     780
gttgattcgg gcgcaaggga caaagcccct gcacagatgc ttgaccctga ttcagggcca     840
aggaactaac gcccagtgct gatggcaacg gttttctgtg cgtaatgttg acattcttca     900
cagcgtgatg ccacctcgca aaaccatctg ctcaatgttt tgtccgctcc acacactggc     960
attgatagga aaacattctc tcacgaagct accgccctc tttccccctc attttttctcc    1020 gcggcctagc ctttacaaag cacctcaata catcaacgat gctgcggcga ctcttcctgc    1080
gctcgtccac ctctctctct cgcaccatcg ccaccatcac gcccggcttg tcccgtgccc    1140
ttgccactct ttctgttggc gcgcccgacc tccctcgtgc ctcgagcacc aacacgaagc    1200
ggcggttcga atggcaagac cccctgatgc tgcgggcgca attgacggag gaagaggca    1260 tgatccaaga catgacccgc gcctactgca aagaaagcct gcaatcccgc atcctccaag    1320
cgaaccgcca cgaggagttt gaccggaaga tcctgacgga aatgggcgag ttgggcttgc    1380
tagggccgac cttaaaaggg tacgatgcc cggagtggg atatgtggca tacgccctga    1440
ttgcccatga ggtggaagcg gtggatagtg cctatcgctc cgcgatgagc gtgcagtctt    1500
ctttggtcat gcatcctatt tatacgttcg gcacggagaa gcagaaggag acgtatttgc    1560
cggggttggc aaagggggacg ttggtgggggt                                   1590
```

```
<210> SEQ ID NO 41
<211> LENGTH: 1550
<212> TYPE: DNA
<213> ORGANISM: Nannochloropsis oculata

<400> SEQUENCE: 41
gacgggcatg attgtgatgg acgacgtaaa agtcccaggg gagaacttat tgccgaaagc      60 caagggggtta ggagggcctt tctcgtgctt gaatagtgcg cggtacggca tctcgtgggg     120
caccatgggg gcggctgggt tttgcatggc tactgcccgg gagtacgtgc tggacaggat     180
gcagtttggg gcgcctttgg caagcaatca gctgatacaa agaaactcg cagacatggg     240 gactgagatt gcgcttggtc tccaggcgtc gttgagggta gggaggttac tggatcagaa     300
agaggccgtg ccggagatga tctcgatggt aaagaggaat aattgtggga aggcgttgga    360
ggtggtgagg gttgcaaggg atatgttggg agggaatgga atctcggacg aatatcatgt    420
gattcgacat gtgatgaatt tggaggcggt taacacctat gaagggactc atgatgtgca    480
tgcgttgata ctggggagag cgataacggg catcccggcg ttcgtgccgc ggaatagcac    540
atttcagtaa gacagcagag gaagaggaaa acatgagaaa ggaagggagg gtgtgagatc    600
gggagagaga gaggaggcat tgaagatgta aatatcatat agcataggcc cgggcgggca    660
gttgtgcatt tgtaccgcgt cggatagctt aggaagttgg cggaagggat ggggcagag     720 gagaagggta cgaggaaaga agtgaaagtt accaaaatcc gctgggcagg tgtgagttgt    780
gtgtaagaaa ggaaagcggg atggaaggga gaaagattgt gaatagctat tccgtgctca    840
caattttcta tgaaacatgt gcactttggc gagtagaaga gatgaaaaat taaacaaaag    900
gtaaagctga tgtacaacca aaggatgagt atgaatgctt acggtacttt aatatctgtc    960
gaggccgagg cctccgaggc caatttccac ttccacaaaa tgaaactctc atacaagcac   1020
tcgaccaaaa tctatgggac acatgtgggc ttgtaatgct cgcaccgcat gtggcctagg   1080
gtttgtgctc ctggctattg tatcaaaacg cttaattctc ccccgctcaa tttttgcagg   1140
ctactggcac aaatcaagca gcctgcaagc acctggagat ggacatccgc cccgcgttga   1200
ggccgttacg cgtcgaacgg tcggcgggac aattttttgcc tatgggcgtc cattcctgat   1260
ataaagtatg acgactagtc gcccgcgaga tggtccgttg tcacccgatt tcttttgctc   1320
atgatttgac gaaggagccg atagaaacat aaaaatgtct tgttcttccg aaggggggccc   1380 tttctttcat acaactacgg catattattg ccagtccgga atgctcgcca cgcatggtct   1440
gcgccgggcc catgagacat cacttctcag ccgcccggcg gtcccccctg gagttgcgat   1500
gaacacccag cgagcatacg ttatataggc taagacacag tgctgccaca              1550

<210> SEQ ID NO 42
<211> LENGTH: 20
<212> TYPE: DNA
<213> ORGANISM: Artificial Sequence
<220> FEATURE:
<223> OTHER INFORMATION: Primer No. 42

<400> SEQUENCE: 42
gaatgcatgc cggccgagaa                                                 20

<210> SEQ ID NO 43
<211> LENGTH: 20
<212> TYPE: DNA
<213> ORGANISM: Artificial Sequence
<220> FEATURE:
<223> OTHER INFORMATION: Primer No. 43
```

<400> SEQUENCE: 43
gtttcaggcg gtggaaagcg                                          20

<210> SEQ ID NO 44
<211> LENGTH: 20
<212> TYPE: DNA
<213> ORGANISM: Artificial Sequence
<220> FEATURE:
<223> OTHER INFORMATION: Primer No. 44

<400> SEQUENCE: 44
aactcggcgc acccaaaaag                                          20

<210> SEQ ID NO 45
<211> LENGTH: 20
<212> TYPE: DNA
<213> ORGANISM: Artificial Sequence
<220> FEATURE:
<223> OTHER INFORMATION: Primer No. 45

<400> SEQUENCE: 45
tgtggcagca ctgtgtctta                                          20

<210> SEQ ID NO 46
<211> LENGTH: 18
<212> TYPE: DNA
<213> ORGANISM: Artificial Sequence
<220> FEATURE:
<223> OTHER INFORMATION: Primer No. 46

<400> SEQUENCE: 46 atgtacccccc agcttagc                                           18

<210> SEQ ID NO 47
<211> LENGTH: 20
<212> TYPE: DNA
<213> ORGANISM: Artificial Sequence
<220> FEATURE:
<223> OTHER INFORMATION: Primer No. 47

<400> SEQUENCE: 47
tctttgcgct ggacccctcg                                          20

<210> SEQ ID NO 48
<211> LENGTH: 20
<212> TYPE: DNA
<213> ORGANISM: Artificial Sequence
<220> FEATURE:
<223> OTHER INFORMATION: Primer No. 48

<400> SEQUENCE: 48
atcgatgaaa tcaatgtctg                                          20

<210> SEQ ID NO 49
<211> LENGTH: 20
<212> TYPE: DNA
<213> ORGANISM: Artificial Sequence
<220> FEATURE:
<223> OTHER INFORMATION: Primer No. 49

<400> SEQUENCE: 49
gagcgactgg ccaaaagtac                                          20

<210> SEQ ID NO 50
<211> LENGTH: 598

<212> TYPE: PRT
<213> ORGANISM: Nannochloropsis oculata

<400> SEQUENCE: 50

```
Met Met Ser Arg Arg Asp Trp Val Gly Val Leu Phe Gly Val Asp
1               5                   10                  15

Lys Ala Val Asp Asp Lys Ser Glu Glu Asn Gly Gly Gln Ala Gly Gly
            20                  25                  30

Ser Met Thr Phe Gly Ala Ser Gln Leu Leu Glu Gly His Thr Thr Glu
            35                  40                  45

Leu Gln Pro Leu Gly Glu Pro Thr Ala Lys Arg Ile Lys Gln Leu Glu
        50                  55                  60

Arg Leu Cys Gln Pro Asp Val Asp Val Ala Lys Glu Leu His Leu Arg
65                  70                  75                  80

Trp Thr Asp Ser Ser Ser Phe Thr Ser Ser Gly Leu Arg Asp Gly
                85                  90                  95

Phe Arg Ala Cys Leu Arg Met Leu Glu Thr Arg Ser Lys Lys Glu Arg
                100                 105                 110

Asp Ile Arg Arg Ile Trp Leu Leu Thr Asn Glu Asp Asp Pro Ser Glu
            115                 120                 125

Pro Asn Asn Pro Ser Gln Val Ile Lys Asp Ala Gln Glu Gly Gly Val
        130                 135                 140

Asp Val Arg Leu Trp His Phe Pro His Pro Asp Gly Arg Asp Phe Asp
145                 150                 155                 160

Glu Arg Lys Leu Tyr Gly Pro Val Leu Ser Ala Ala Ser Lys Gln Pro
                165                 170                 175

Phe Glu Leu Asp Tyr Ile Lys Ala Asp Glu Glu Thr Glu Ser Glu
                180                 185                 190

Ser Lys Met Val Asn Val Gly Ser Gly Asp Met Thr Thr Leu Leu Gly
            195                 200                 205

Ala Ala Lys Gly Arg Leu Phe Lys Lys Arg Tyr Ala Cys Thr Ile
        210                 215                 220

Trp Gln Val Thr Asp Ser Pro Pro Leu Ser Ile Asn Val Ala Leu Tyr
225                 230                 235                 240

Lys Thr Ile Gln Pro Cys Lys Lys Pro Thr Pro Val Gln Leu Ala Ala
                245                 250                 255

Ala Thr Asn Arg Arg Leu Val Pro Ser Thr Lys Trp Leu Cys Glu Glu
            260                 265                 270

Leu Val Gln Tyr Ile Asp Leu Glu Leu Glu Ala Ala Tyr Gly Leu Asp
        275                 280                 285

Phe Gly Ser Ser Asn Thr Thr Val Pro Phe Lys Arg Pro Glu Phe Glu
    290                 295                 300

Tyr Thr Leu Arg Ala Gly Leu Ser Glu Pro Gly Leu Tyr Leu Leu Gly
305                 310                 315                 320

Phe Val Pro Ser Glu Glu Leu Ala Trp Glu Leu Asn Val Thr Ser Ser
                325                 330                 335

Thr Thr Val Tyr Pro Glu Glu Leu Ser Leu Lys Gly Cys Thr Arg Ala
            340                 345                 350

Phe Ile Ser Leu Arg Glu Ala Met Leu Lys Arg Glu Arg Met Ala Val
        355                 360                 365

Val Arg Tyr Gln Ala Ser Ala Lys Ser Glu Pro Arg Leu Ala Val Leu
    370                 375                 380

Leu Ala Ser Leu Ala Thr Lys Gly Leu Glu Leu Val Glu Leu Pro Phe
385                 390                 395                 400
```

```
Leu Gly Asp Leu Arg Ser Val Glu Ser Pro His Leu Asp Cys Pro Pro
            405                 410                 415

Pro Pro Pro Glu Lys Glu Gln Leu Glu Ala Ala Arg Lys Val Val Ala
        420                 425                 430

Arg Leu Thr Leu Lys Pro Gln Gln Tyr Ser Val Gly Phe Asn Asn Pro
            435                 440                 445

Ala Leu Glu Lys Phe Tyr Ser Gly Leu Gln Ala Leu Ala Leu Glu Glu
        450                 455                 460

Ala Lys Thr Glu Trp Asn Glu Ile Thr Asp Asp Ser Thr Trp Pro Ser
465                 470                 475                 480

Asp Glu Leu Leu Gly Arg Ala Glu Glu Leu Glu Glu Leu Trp Glu
            485                 490                 495

Leu Ser Pro Asp Pro Arg Lys Gly Val Gln Arg Gly Arg Gly Arg Lys
            500                 505                 510

Arg Lys Ala Asp Ala Val Thr Lys Thr Val Lys Gly Lys Leu Val Ala
        515                 520                 525

Glu Lys Val Ser Lys Ala Glu Asp Gly Asp Glu Lys Ile Gly Gly
        530                 535                 540

Gly Gly Asp Arg Ser Val Lys Asp Leu Ser Met Gly Lys Leu Ala Lys
545                 550                 555                 560

Leu Thr Val Pro Gln Leu Lys Glu Ile Cys Arg Ala Arg Gly Leu Pro
            565                 570                 575

Val Ser Gly Lys Lys Gly Asp Ile Ile Asp Arg Leu Gln Met Asp Leu
            580                 585                 590

Glu Thr Asp Asp Asp Leu
        595

<210> SEQ ID NO 51
<211> LENGTH: 1797
<212> TYPE: DNA
<213> ORGANISM: Nannochloropsis oculata

<400> SEQUENCE: 51
atgatgagtc gtcgggactg ggtcggagtt gtgcttttcg gggtagataa ggcagtggat      60
gataagtcgg aggaaaatgg cggccaagca ggaggttcga tgacattcgg cgccagccaa     120
ttgcttgagg ccatacgac cgagttgcaa cccttggggg aaccgaccgc caaacgcatc      180
aagcaactgg agcggctgtg ccaacccgac gtcgatgttg ccaaggaatt gcatttaagg     240
tggacagact cctcctcttt tacctcttca tccggcttac gggacgggtt ccgagcgtgt     300
ctgcggatgc tggagacccg gtccaaaaag gaacgggaca ttcggcgcat ctggcttctc     360
accaacgagg acgacccctc ggagcccaac aacccaagcc aagtaataaa agatgcccaa     420
gagggagggg tggatgtacg cttgtggcat tttcctcatc ccgacggccg ggatttcgac     480
gagcgaaagc tttatgggcc cgtgctctcc gccgcgagta agcagccctt cgaactagac     540
tacatcaagg cagacgagga agagaccgag tccgagtcga agatggtaaa tgtcgggagc     600
ggggacatga caactctgct gggggcagcc aagggtcgac tatttaagaa gcgtcgctac     660
gcctgcacca tctggcaagt tactgactcg cctccctct ccatcaacgt tgcccttta      720 aagaccatcc aaccctgtaa aaacccacg cccgtgcagc tggccgcggc tacaaatcga     780
cggctagttc cgagcaccaa gtggctatgt gaggagctgg tgcaatacat tgacttggag     840
ctggaggcag cttacggcct tgacttcggg tcctccaaca ccaccgtccc cttcaaacgc     900
cctgagtttg aatacaccct ccgcgctggt cttagcgagc ccgggctcta tttgctggga     960
```

```
tttgtgccct ctgaggagct ggcatgggag ctgaacgtga cgagcagcac gacggtctac    1020
ccagaagagc tctcgctcaa gggttgcact cgtgccttca tctccctgcg ggaggcgatg    1080
ctgaagcgtg agcggatggc agtggtccgg tatcaggcgt cggcaaagtc agagcctcgt    1140
ctagctgtgc tacttgcttc attggcaacc aagggtttag aattggttga gttgcctttc    1200
ttgggcgatc tgcgttctgt ggagagcccg catctggact gtcccccgcc gccgccggag    1260
aaagaacagc tggaggcagc taggaaggtg gtggcgcgct tgactttaaa gccacagcag    1320
tactctgtgg gcttcaataa tccggccttg gaaaagtttt actcgggttt gcaggcgttg    1380
gcgctggagg aggcaaagac ggagtggaat gagataacgg atgacagcac ctggccctcg    1440
gacgagttgc ttggccgagc agaagaagag ttggaggagc tgtgggaact gtctcctgat    1500
ccaagaaagg gtgtgcagag ggggaggggg aggaagcgga aggcagatgc agtgacgaaa    1560
actgttaagg gtaagctggt cgctgagaag gtcagcaagg ctgaagacga ggatgatgag    1620
aagataggag gcggtggcga tagatcggtg aaggaccttt cgatgggaaa gctggccaaa    1680
ctgacggttc ctcaactgaa ggagatctgt cgtgcacgtg ggttgcccgt gtcaggcaag    1740
aagggagaca tcatcgatcg tttacagatg gacctcgaga ccgatgatga cttgtga       1797
```

US 11,306,320 B2

METHOD FOR PROMOTING HOMOLOGOUS RECOMBINATION

FIELD OF THE INVENTION

The present invention relates to a method of producing a transformant.

BACKGROUND OF THE INVENTION

In recent years, researches and developments on renewable energy have been promoted toward realization of a sustainable society. In particular, photosynthetic microorganisms are expected as biofuel organisms without competing with grain in addition to an effect on reducing carbon dioxide.

Among them, microalgae belonging to the genus *Nannochloropsis* or the like attract attention due to its usefulness in biofuel and food material production. The microalgae can produce lipids that can be used as the biodiesel fuels and the food materials through photosynthesis. Further, the microalgae attract attention as next-generation biomass resources, because the microalgae do not compete with foods.

As seen from the aforesaid background, research on modifying various genes present in genomic DNA is being actively conducted with regard to microalgae. For example, Non-Patent Literature 1 discloses that a targeted gene can be knocked out by homologous recombination in the oil-producing *Nannochloropsis* sp.

"Homologous recombination" is a type of DNA repair mechanism, which occurs in a portion having closely resembling homologous sequences on both strands of double-stranded DNA.

However, homologous recombination does not always occur and non-homogenous recombination also occurs at a certain frequency (see Non-Patent Literature 1). Accordingly, in order to efficiently modify various genes present in a desired region on a genome, it is important to elevate probability of acquiring a transformant in which homologous recombination occurs, by reducing frequency at which plasmids or DNA cassettes introduced for homologous recombination come to be incorporated into the genome by non-homogenous recombination at a site different from the targeted genome site.

In human, yeast or animal cells, research is advancing on a protein related to non-homogenous recombination or a gene encoding the protein (for example, see Patent Literature 1 and Non-Patent Literature 2). However, in algae belonging to the genus *Nannochloropsis*, neither the protein related to non-homogenous recombination nor the gene encoding the protein is identified yet.

CITATION LIST

Patent Literatures

Patent Literature 1: WO 2005/083090 A1

Non-Patent Literatures

Non-Patent Literature 1: Oliver Kiliana, et al., Proc. Natl. Acad. Sci. USA, 2011, vol. 108(52), p. 21265-21269
Non-Patent Literature 2: Takashi Ochil, et al., Science, 2015, Vol. 347, Issue 6218, p. 185-188

SUMMARY OF THE INVENTION

The present invention relates to a method of producing a transformant, which contains using an alga belonging to the genus *Nannochloropsis* as a host, wherein function of the following protein (A) or (B) of the alga is suppressed, inhibited or deleted:

(A) a protein consisting of the amino acid sequence set forth in SEQ ID NO: 50; and
(B) a DNA binding protein consisting of an amino acid sequence having 70% or more identity with the amino acid sequence of the protein (A).

Moreover, the present invention relates to a method of producing a host, which contains suppressing, inhibiting or deleting function of the protein (A) or (B) in an alga belonging to the genus *Nannochloropsis*,
wherein the host is used for preparing a transformant, in which arbitrary modification is performed by homologous recombination in a targeted site of genomic DNA of the alga.

Moreover, the present invention relates to an alga belonging to the genus *Nannochloropsis* in which function of the protein (A) or (B) is suppressed, inhibited or deleted.

Further, the present invention relates to a method of preparing a transformant, which contains performing arbitrary modification by homologous recombination in a targeted site of genomic DNA of an alga, wherein the alga is used as a host.

Other and further objects, features and advantages of the invention will appear more fully from the following description, appropriately referring to the accompanying drawings.

BRIEF DESCRIPTION OF DRAWINGS

FIG. 1(*b*) is a schematic diagram showing an insert sequence of a plasmid for homologous recombination of the gene encoding the protein (A) or (B), prepared in Example 1.

FIG. 2(*b*) is a schematic diagram for comparing sizes of DNA fragments to be amplified for confirming introduction of the cassette for homologous recombination between the wild-type strain of *Nannochloropsis oculata* and the deficient strain of the gene encoding the protein (A) or (B).

FIG. 3(*b*) is a schematic diagram showing an insert sequence of a plasmid for homologous recombination of the ACDH1 gene, prepared in Example 2.

FIG. 4(*b*) is a schematic diagram showing an insert sequence of a plasmid for homologous recombination of the ACDH2 gene, prepared in Example 2.

FIG. 5(*b*) is a schematic diagram for comparing sizes of DNA fragments to be amplified for confirming introduction of a cassette for homologous recombination between a wild-type strain of Nannochloropsis oculata or a deficient strain of the gene encoding the protein (A) or (B) and the homologous recombinant strain of genome around the ACDH1 gene.

DESCRIPTION OF EMBODIMENTS

Figure 1A:
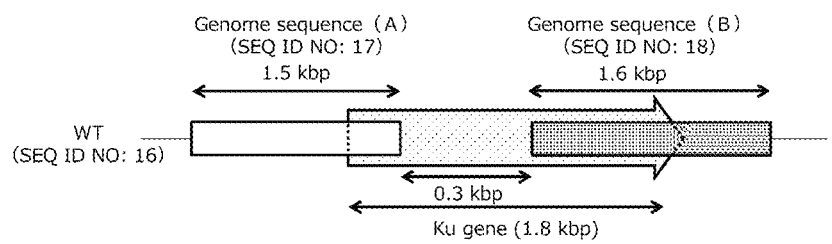
FIG. 1(*a*) is a diagram schematically showing a genome sequence around a gene encoding the protein (A) or (B) in a wild-type strain of *Nannochloropsis oculata*.

The present invention relates to providing a method of producing transformants of algae belonging to the genus Nannochloropsis, in which non-homologous recombination is inhibited and homologous recombination occurs.

Further, the present invention relates to providing algae belonging to the genus Nannochloropsis, in which probability of occurrence of homologous recombination is improved.

As mentioned above, in order to efficiently modify various genes in a genome, it is important to reduce frequency of non-homologous recombination so as to elevate probability of acquiring transformants in which homologous recombination occurs. However, almost no report has been made regarding suppressing non-homologous recombination or improving frequency of homologous recombination in algae belonging to genus Nannochloropsis.

Accordingly, the present inventors diligently continued research regarding this issue and, as a result, newly identified a protein related to non-homologous recombination in algae belonging to the genus Nannochloropsis. Then, by using as host algae in which function of the newly identified protein related to non-homologous recombination is suppressed, inhibited or deleted, the present inventors found that frequency of non-homologous recombination in the algae is reduced (or probability of occurrence of homologous recombination is elevated), and probability of acquiring transformants in which homologous recombination occurs is markedly improved.

The present invention has been achieved on the basis of these findings.

In the algae belonging to the genus Nannochloropsis used in the present invention, occurrence of non-homologous recombination is inhibited and the probability of occurrence of homologous recombination is significantly improved. Thus, according to the present invention, the occurrence of non-homologous recombination can be inhibited, and the probability of acquiring a transformant in which homologous recombination occurs can be improved.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in the present specification, the "stringent conditions" includes, for example, the method described in Molecular Cloning—A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a site of 5' end side or a region subsequent to 5' end side of a targeted gene or region, and not a position from a translational initiation site. On the other hand, the term "downstream" of the gene means a site of 3' end side or a region subsequent to 3' end side of the targeted gene or region.

In the present invention, algae belonging to the genus Nannochloropsis in which function of the protein (A) or (B) is suppressed, inhibited or deleted are used as hosts for preparation of transformants. The protein (A) and (B) are one kind of a protein involved in non-homologous recombination, derived from the algae belonging to the genus Nannochloropsis.

The above-mentioned "non-homologous recombination" is one of the DNA repair mechanisms known as non-homologous end-joining repair. In non-homologous end-joining repair, Ku, which is a DNA binding protein, first binds to DNA ends resulting from a DNA double strand break to protect the DNA ends. Then, DNA-dependent kinase binds to the DNA ends through the Ku protein to form complexes composed of the DNA, the Ku protein and the DNA-dependent kinase, and the complexes are paired with each other. In the vicinity of the complexes, ligase complexes composed of DNA ligase IV, XRCC4 and XLF are assembled, and the DNA ends are relinked by action of the ligase complexes, whereby non-homologous end-joining repair is completed. Thus, when the DNA ends are relinked, the DNA is repaired in non-homologous recombination without depending on homology of nucleotide sequences in the vicinities of the DNA ends, which is different from homologous recombination. Therefore, when gene cassettes containing nucleotide sequence homologous with genomic DNA in a targeted site are used, unlike in homologous recombination that can introduce gene cassettes into a desired genome site, in non-homologous recombination, homologous sequences are not recognized and gene cassettes are nonspecifically introduced into the genomic DNA.

The protein (A) or (B) is a protein involved in such non-homologous end-joining repair. In the present invention, the function of the protein (A) or (B) is suppressed, inhibited or deleted, whereby the occurrence of non-homologous recombination is suppressed or inhibited when plasmids or DNA cassettes for homologous recombination is introduced into the algae, thereby improving probability of acquiring transformants in which homologous recombination occurs.

In the algae in which function of the protein (A) or (B) is suppressed, inhibited or deleted, the probability of occurrence of homologous recombination is improved, as compared with a wild-type strain. The term "wild-type strain" means algae in which function of the protein (A) or (B) is not suppressed or inhibited.

The algae used in the present invention are the algae belonging to the genus Nannochloropsis. The algae belonging to the genus Nannochloropsis are small algae (microalgae) having a spherical or elliptical shape and a size of about 2 to 5 μm.

The algae used in the present invention can be appropriately selected from the algae which have a gene encoding the protein (A) or (B) and can perform homologous recombination. In the present invention, a gene encoding the protein (A) or (B) is preferably present on the genome of the algae.

Specific examples of the algae belonging to the genus *Nannochloropsis* to be used in the present invention include *Nannochloropsis oculata, Nannochloropsis gaditana, Nannochloropsis salina, Nannochloropsis oceanica, Nannochloropsis atomus, Nannochloropsis maculata, Nannochloropsis granulata*, and *Nannochloropsis* sp. Among these, *Nannochloropsis oculata* or *Nannochloropsis gaditana* is preferred, and *Nannochloropsis oculata* is more preferred.

The protein (A) or (B) is a protein involved in non-homologous recombination, and from the results of Blast of amino acid sequences and nucleotide sequences, is considered to be a kind of Ku protein, which is the DNA binding protein. That is, the protein (A) or (B) has the function of the Ku protein. Here, a term "function of the Ku protein" means capability to recognize the DNA ends resulting from DNA double strand break, and to bind and protect the recognized DNA ends. It does often a function of linking the DNA-dependent kinase with the DNA ends. Then, a term "function of the protein (A) or (B)" means capability to recognize the DNA ends resulting from DNA double strand break, to bind the recognized DNA ends and recruit the DNA-dependent kinase at the DNA ends. Hereinafter, in the present specification, the protein (A) or (B) is also referred to merely as "Ku" or "NoKu".

A protein consisting of the amino acid sequence set forth in SEQ ID NO: 50 is a protein having the function of the Ku protein, derived from a *Nannochloropsis oculata* strain NIES-2145, which is the alga belonging to the genus *Nannochloropsis*. In addition, *Nannochloropsis oculata* strain NIES-2145 can be obtained from National Institute for Environmental Studies (NIES).

The protein (B) is a protein consisting of an amino acid sequence having 70% or more identity with the amino acid sequence of the protein (A), and having the function of the Ku protein.

In general, it is known that an amino acid sequence encoding a protein does not necessarily function unless the sequence in the whole region is conserved, and there exists a region in which the protein function is not influenced even if the amino acid sequence is changed. In such a region which is not essential to the protein function, even if the mutation of the amino acid, such as deletion, substitution, insertion and addition thereof is introduced thereinto, the function inherent to the protein can be maintained. In the protein specified in the present invention, the protein (B) also includes a protein in which the function of the Ku protein is thus retained and the amino acid sequence partially undergoes mutation.

In the protein (B), the identity with the amino acid sequence of the protein (A) is preferably 75% or more, more preferably 80% or more, further preferably 85% or more, further preferably 90% or more, further preferably 92% or more, further preferably 95% or more, further preferably 98% or more, and furthermore preferably 99% or more, in view of the function of the Ku protein. Further, specific examples of the protein (B) include a protein in which 1 or several (for example 1 or more and 180 or less, preferably 1 or more and 150 or less, more preferably 1 or more and 120 or less, further preferably 1 or more and 90 or less, furthermore preferably 1 or more and 60 or less, furthermore preferably 1 or more and 48 or less, furthermore preferably 1 or more and 30 or less, furthermore preferably 1 or more and 12 or less, and furthermore preferably 1 or more and 6 or less) amino acids are deleted, substituted, inserted or added to the amino acid sequence of the protein (A).

An example of the gene encoding the protein (A) or (B) (NoKu) includes a gene consisting of the following DNA (a) or (b) (hereinafter, also referred to as "Ku gene" or "NoKu gene"):
(a) a DNA consisting of the nucleotide sequence set forth in SEQ ID NO: 51; and
(b) a DNA consisting of a nucleotide sequence having 55% or more identity with the nucleotide sequence of the DNA (a), and encoding a DNA binding protein.

The nucleotide sequence set forth in SEQ ID NO: 51 is a nucleotide sequence of a gene encoding the protein consisting of the amino acid sequence set forth in SEQ ID NO: 50 (the protein (A)).

In the DNA (b), the identity with the nucleotide sequence of the DNA (a) is preferably 60% or more, more preferably 65% or more, further preferably 70% or more, further preferably 75% or more, further preferably 80% or more, further preferably 85% or more, further preferably 90% or more, further preferably 92% or more, further preferably 95% or more, further preferably 98% or more, and furthermore preferably 99% or more, in view of the function of the Ku protein.

Further, the DNA (b) is also preferably a DNA in which 1 or several (for example 1 or more and 809 or less, preferably 1 or more and 719 or less, more preferably 1 or more and 629 or less, further preferably 1 or more and 540 or less, further preferably 1 or more and 450 or less, further preferably 1 or more and 360 or less, further preferably 1 or more and 270 or less, further preferably 1 or more and 180 or less, further preferably 1 or more and 144 or less, further preferably 1 or more and 90 or less, further preferably 1 or more and 36 or less, and furthermore preferably 1 or more and 18 or less) nucleotides are deleted, substituted, inserted or added to the nucleotide sequence of the DNA (a), and encoding the DNA binding protein.

Furthermore, the DNA (b) is also preferably a DNA capable of hybridizing with a DNA consisting of the nucleotide sequence complementary with the DNA (a) under a stringent condition, and encoding the DNA binding protein.

In the present invention, a method of suppressing, inhibiting or deleting function of the NoKu can be appropriately selected from among ordinary methods. Specific examples thereof include a method of deleting or inactivating a NoKu gene, a method of downregulating a NoKu gene, a method of weakening function of a NoKu protein by deficiency of the NoKu protein per se or introduction of mutation thereinto, addition of a drug thereinto, or the like, a method of modifying a promoter of a NoKu gene, and a method of utilizing a genome editing technology such as antisense and promoter competition. Above all, it is preferable to suppress, inhibit or delete function of the NoKu by deleting or inactivating the NoKu gene, or downregulating the NoKu gene.

A method of suppressing, inhibiting or deleting function of the NoKu protein by deleting or inactivating Noku gene will be described.

The NoKu gene of the algae is deleted or inactivated, whereby expression of the Ku protein which binds to the DNA ends generated by the DNA double strand break is inhibited and occurrence of non-homologous end-joining repair (non-homologous recombination) is suppressed or inhibited. As a result, frequency of non-homologous recombination in the algae is reduced. Accordingly, when transformation is performed by using, as the host, the algae in which the NoKu gene is deleted or inactivated, the probability of acquiring the transformant in which homologous recombination occurs is improved.

A method of deleting or inactivating the NoKu gene can be appropriately selected from ordinary methods. For example, according to general methods such as a gene disruption method utilizing homologous recombination capability of the algae per se, a method utilizing a genome editing technology such as Transcription activator-like effector nuclease (TALEN) and Clustered Regularly Interspaced Short Palindromic Repeat (CRISPR), and a mutagenesis method utilizing mutation or the like, the NoKu gene can be deleted or inactivated.

Specifically, DNA fragments containing a part of the NoKu gene or a circular recombinant plasmid obtained by cloning the DNA fragments into a suitable plasmid (vector) is incorporated into cells of the microalgae, and by homologous recombination in a partial region of the NoKu gene, the NoKu gene on the genome can be deleted, or inactivated by splitting the NoKu gene.

Moreover, according to a method of inducing mutation of the NoKu gene by use of a mutagen such as N-methyl-N'-nitro-N-nitrosoguanidine, or irradiation with ultraviolet light, gamma rays or the like, a method of inducing site-specific point mutation (for example, frameshift mutation, in-frame mutation, insertion of a termination codon, or the like) into the NoKu gene (for example, a site important for expressing the function of the Ku), a method of wholly or partially replacing the NoKu gene by other arbitrary DNA fragment (for example, an arbitrary selection marker), or the like, the Ku gene can be randomly inactivated.

In the present invention, the NoKu gene on the genome is preferably deleted or inactivated by homologous recombination.

When the NoKu gene is deleted or inactivated by homologous recombination, the plasmid for homologous recombination or the DNA cassette for homologous recombination of the NoKu gene is introduced into the algae.

In the plasmid for homologous recombination or the DNA cassette for homologous recombination of the NoKu gene used herein, the NoKu gene is wholly or partially applied as a targeted region. Then, it is preferable to construct the plasmid or the DNA cassette having a nucleotide sequence homologous with a part of the upstream side of the genome encoding the targeted region, and a nucleotide sequence homologous with a part of the downstream side of the genome to introduce the resultant material into the algae.

Moreover, in order to select a strain in which the plasmid for homologous recombination or the DNA cassette for homologous recombination is incorporated into the cells, the selection marker to be constructed into the plasmid for homologous recombination or the DNA cassette for homologous recombination can be appropriately selected from the selection markers ordinarily used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

The plasmid for homologous recombination or the DNA cassette for homologous recombination to be used for deleting or inactivating the NoKu gene can be prepared by using the plasmid (vector) ordinarily used for introducing the DNA fragments into the algae. Specific examples of the plasmid that can be used include pUC19 (manufactured by Takara Bio), pUC118 (manufactured by Takara Bio), P66 (Chlamydomonas Center), P-322 (Chlamydomonas Center), pPha-T1 (see Yangmin Gong, et al., Journal of Basic Microbiology, 2011, vol. 51, p. 666-672) and pJET1 (manufactured by COSMO BIO). In particular, pUC19, pUC118, pPha-T1 or pJET1 is preferably used.

Introduction of the selection marker to the vector can be conducted by an ordinary technique such as restriction enzyme treatment and ligation.

A size of the plasmid for homologous recombination or the DNA cassette for homologous recombination used for deletion or inactivation of the NoKu gene can be appropriately set in consideration of introduction efficiency into the algae, homologous recombination efficiency, and the like. For example, the size of the nucleotide sequence upstream or downstream of the targeted region to be used as the homologous sequence is preferably 300 bp or more, and more preferably 500 bp or more for each. Moreover, an upper limit thereof is preferably 2.5 kbp, and more preferably 2 kbp.

A transformation method for introducing the plasmid for homologous recombination or the DNA cassette for homologous recombination into the algae can be appropriately selected from ordinary methods according to a kind of the algae, or the plasmid for homologous recombination or the DNA cassette for homologous recombination of the NoKu gene. Examples of the method for transformation include a transformation method of using calcium ion, a general competent cell transformation method, a protoplast transformation method, an electroporation method, an LP transformation method, a method of using Agrobacterium, a particle gun method, and the like. In addition, transformation can also be performed in the present invention by using the electroporation method described in Randor Radakovits, et al., Nature Communications, DOI: 10.1038/ncomms1688, 2012, or the like.

The algae in which the NoKu gene is deleted or inactivated can be selected by utilizing the selection marker or the like. For example, the selection can be carried out by using an indicator whether an alga acquires the drug resistance as a result of introducing a drug resistance gene into a host cell. Further, the introduction of a target DNA fragment can also be confirmed by PCR method using a genome as a template or the like.

A method of downregulating the NoKu gene to suppress, inhibit or delete the function of the NoKu will be described.

Expression of the NoKu gene is suppressed, or the promoter located upstream of the NoKu gene is identified, and is deleted or inactivated, whereby an expression level of the NoKu gene is reduced (downregulation of the NoKu gene). When the expression level of the NoKu gene is reduced, the expression of the Ku protein which binds to the DNA ends generated by the DNA double strand break is inhibited, and the occurrence of non-homologous end-joining repair (non-homologous recombination) is suppressed or inhibited. As a result, frequency of non-homologous recombination in the algae is reduced. Accordingly, when transformation is performed by using, as the host, the algae in which the expression of the NoKu gene is suppressed, or the promoter located upstream of the NoKu gene is deleted or inactivated, the probability of acquiring the transformant in which homologous recombination occurs is improved.

The method of downregulating the NoKu gene can be appropriately selected from ordinary methods. Specific examples thereof include a method of inducing mutation of a promoter sequence or a transcription and translation initiation region of a NoKu gene by a mutagen such as N-methyl-N'-nitro-N-nitrosoguanidine, or irradiation with UV, gamma rays or the like, a method of inserting other arbitrary DNA fragments (for example, an arbitrary repressor, an arbitrary selection marker or the like) into a promoter sequence or a transcription and translation initiation region of a NoKu gene, a method of wholly or partially replacing a promoter sequence or a transcription and translation initiation region of a NoKu gene by other arbitrary DNA fragment (for example, an arbitrary repressor, an arbitrary selection marker or the like), an antisense method, an RNA interference method and promoter competition.

The algae in which the function of the NoKu is suppressed, inhibited or deleted can be preferably used for preparation of the transformant into which the plasmid or the DNA cassette for homologous recombination containing an arbitrary DNA sequence, either a foreign gene or an endogenous gene, is introduced, to perform arbitrarily modification in the targeted site of the genomic DNA by homologous recombination. As mentioned above, in the algae of the present invention, frequency of non-homologous recombination is reduced. Accordingly, when the algae are used as the host, the probability capable of acquiring the transformant in which homologous recombination occurs is significantly high, and the transformant in which arbitrary modification is performed in the targeted site of the genomic DNA can be efficiently prepared.

More specifically, homologous recombination occurs at a high frequency by using the algae in which the function of the NoKu is suppressed, inhibited or deleted, and the transformant in which an arbitrary gene is incorporated into the targeted site of an objective genomic DNA can be efficiently prepared.

Alternatively, in the algae in which the function of the NoKu is suppressed, inhibited or deleted, homologous recombination occurs with high probability. Accordingly, the arbitrary gene is also easily disrupted by homologous recombination by targeting the arbitrary gene encoded on the genome of the algae.

Specifically, the plasmid or the DNA cassette for homologous recombination, having nucleotide sequences highly homologous with each of a 5' end side region and a 3' end side region outside a modification targeted region on the genome of the algae of the present invention is introduced into the algae of the present invention to allow homologous recombination to occur between the genome and the plasmid or the DNA cassette for homologous recombination, whereby the transformant in which modification of the genomic DNA, such as disruption (splitting, substitution or the like) of a specific DNA sequence and introduction of a desired gene, is performed can be efficiently prepared.

The present invention also provides a plasmid for homologous recombination or a DNA cassette for homologous recombination of a NoKu gene, containing a nucleotide sequence homologous with a part of the upstream side of a region consisting of a nucleotide sequence of the NoKu gene on a genome and a nucleotide sequence upstream thereof, and a nucleotide sequence homologous with a part of the downstream side of a region consisting of a nucleotide sequence of the NoKu gene on the genome and a nucleotide sequence downstream thereof. This plasmid for homologous recombination or this DNA cassette for homologous recombination can be preferably used for preparation of the algae in which the above-described function of the NoKu is suppressed, inhibited or deleted.

With regard to the embodiments described above, the present invention also discloses methods, algae, proteins, genes, plasmid vectors or DNA cassettes, and methods of preparing transformants, described below.

<1> A method of improving probability of acquiring a transformant in which homologous recombination occurs, which contains performing transformation by using, as a host, an alga belonging to the genus *Nannochloropsis*, wherein function of the following protein (A) or (B) of the alga is suppressed, inhibited or deleted:

(A) a protein consisting of the amino acid sequence set forth in SEQ ID NO: 50; and (B) a DNA binding protein consisting of an amino acid sequence having 70% or more, preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence of the protein (A).

<2> A method of producing a transformant, which contains using an alga belonging to the genus *Nannochloropsis* as a host, wherein function of the protein (A) or (B) of the alga is suppressed, inhibited or deleted.

<3> A method of producing a host, which contains suppressing, inhibiting or deleting function of the protein (A) or (B) in an alga belonging to the genus *Nannochloropsis*, wherein the host is used for preparation of a transformant, in which arbitrary modification is performed by homologous recombination in a targeted site of genomic DNA of the alga.

<4> The method described in any one of the above items <1> to <3>, wherein a gene encoding the protein (A) or (B) is deleted or inactivated or a gene encoding the protein (A) or (B) is downregulated, to suppress, inhibit or delete the function of the protein (A) or (B).

<5> A method of improving probability of acquiring a transformant in which homologous recombination occurs, which contains performing transformation by using, as a host, an alga belonging to the genus *Nannochloropsis*, wherein a gene encoding the protein (A) or (B) of the alga is deleted or inactivated, or a gene encoding the protein (A) or (B) of the alga is downregulated.

<6> A method of producing a transformant, which contains using, as a host, an alga belonging to the genus *Nannochloropsis*, wherein a gene encoding the protein (A) or (B) of the alga is deleted or inactivated, or a gene encoding the protein (A) or (B) of the alga is downregulated.

<7> A method of producing a host, which contains deleting or inactivating a gene encoding the protein (A) or (B), or downregulating a gene encoding the protein (A) or (B), in an alga belonging to the genus *Nannochloropsis*; wherein the host is used for preparation of a transformant, in which arbitrary modification is performed by homologous recombination in a targeted site of genomic DNA of the alga.

<8> The method described in any one of the above items <1> to <7>, wherein probability of occurrence of homologous recombination of the host is improved, as compared with a wild-type strain of the alga.

<9> The method described in any one of the above items <1> to <8>, wherein the protein (B) consists of an amino acid sequence in which 1 or several, preferably 1 or more and 180 or less, more preferably 1 or more and 150 or less, further preferably 1 or more and 120 or less, furthermore preferably 1 or more and 90 or less, furthermore preferably 1 or more and 60 or less, furthermore preferably 1 or more and 48 or less, furthermore preferably 1 or more and 30 or less, furthermore preferably 1 or more and 12 or less, and furthermore preferably 1 or more and 6 or less amino acids are deleted, substituted, inserted or added to the amino acid sequence of the protein (A).

<10> The method described in any one of the above items <1> to <9>, wherein the gene encoding the protein (A) or (B) is a gene consisting of the following DNA (a) or (b):
(a) a DNA consisting of the nucleotide sequence set forth in SEQ ID NO: 51; and
(b) a DNA consisting of a nucleotide sequence having 55% or more, preferably 60% or more, more preferably 65% or more, further preferably 70% or more, furthermore preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence of the DNA (a), and encoding a DNA binding protein.

<11> The method described in the above item <10>, wherein the DNA (b) is a DNA consisting of a nucleotide sequence in which 1 or several, preferably 1 or more and 809 or less, more preferably 1 or more and 719 or less, further preferably 1 or more and 629 or less, furthermore preferably 1 or more and 540 or less, furthermore preferably 1 or more and 450 or less, furthermore preferably 1 or more and 360 or less, furthermore preferably 1 or more and 270 or less, furthermore preferably 1 or more and 180 or less, furthermore preferably 1 or more and 144 or less, furthermore preferably 1 or more and 90 or less, furthermore preferably 1 or more and 36 or less, and furthermore preferably 1 or more and 18 or less nucleotides, are deleted, substituted, inserted or added to the nucleotide sequence of the DNA (a), and encoding a DNA binding protein, or a DNA capable of hybridizing with a DNA consisting of the nucleotide sequence complementary with the DNA (a) under a stringent condition, and encoding a DNA binding protein.

<12> The method described in any one of the above items <1> to <11>, wherein the alga is an alga selected from the group consisting of *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis qranulata*, and *Nannochloropsis* sp., preferably *Nannochloropsis oculata* or *Nannochloropsis gaditana*, more preferably *Nannochloropsis oculata*, or further preferably *Nannochloropsis oculata* strain NIES-2145.

<13> The method described in any one of the above items <1> to <12>, wherein the protein (A) or (B) is a protein which recognizes DNA ends generated by DNA double strand break, and binds to the DNA ends recognized to recruit DNA-dependent kinase to the DNA ends.

<14> An alga belonging to the genus *Nannochloropsis*, in which function of the protein (A) or (B) is suppressed, inhibited or deleted.

<15> The alga described in the above item <14>, wherein the function of the protein (A) or (B) is suppressed, inhibited or deleted by deleting or inactivating the gene encoding the protein (A) or (B), or by downregulating the gene encoding the protein (A) or (B).

<16> An alga belonging to the genus *Nannochloropsis*, in which a gene encoding the protein (A) or (B) is deleted or inactivated, or a gene encoding the protein (A) or (B) is downregulated.

<17> The alga described in any one of the above items <14> to <16>, wherein probability of occurrence of homologous recombination in the alga is improved, as compared with that of a wild-type strain of the alga.

<18> The alga described in any one of the above items <14> to <17>, wherein the protein (B) is a protein specified in the above item <9>.

<19> The alga described in any one of the above items <14> to <18>, wherein the gene encoding the protein (A) or (B) is a gene consisting of the DNA (a) or (b).

<20> The alga described in the above item <19>, wherein the DNA (b) is a DNA specified in the above item <11>.

<21> The alga described in any one of the above items <14> to <20>, wherein the alga is an alga selected from the group consisting of *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp., preferably *Nannochloropsis oculata* or *Nannochloropsis gaditana*, more preferably *Nannochloropsis oculata*, or further preferably *Nannochloropsis oculata* NIES-2145 strain.

<22> The alga described in any one of the above items <14> to <21>, wherein the protein (A) or (B) is a protein which recognizes DNA ends generated by DNA double strand break, and binds to the DNA ends recognized to recruit DNA-dependent kinase to the DNA ends.

<23> The protein (A) or (B).

<24> A gene encoding the protein (A) or (B).

<25> The protein or gene described in the above item <23> or <24>, wherein the protein (B) is a protein specified in the above item <9>.

<26> A gene consisting of the DNA (a) or (b).

<27> The gene described in the above item <26>, wherein the DNA (b) is a DNA specified in the above item <11>.

<28> A plasmid for homologous recombination or a DNA cassette for homologous recombination of a gene encoding the protein (A) or (B), containing:
  a nucleotide sequence homologous with a part of the upstream side of a region consisting of a nucleotide sequence of the gene encoding the protein (A) or (B) on a genome of algae belonging to the genus *Nannochloropsis*, and a nucleotide sequence upstream thereof; and
  a nucleotide sequence homologous with a part of the downstream side of a region consisting of a nucleotide sequence of the gene encoding the protein (A) or (B) on the genome, and a nucleotide sequence downstream thereof.

<29> The plasmid or the DNA cassette described in the above item <28>, wherein the protein (B) is a protein specified in the above item <9>.

<30> The plasmid or the DNA cassette described in the above item <28> or <29>, wherein the gene encoding the protein (A) or (B) is a gene consisting of the DNA (a) or (b).

<31> The plasmid or the DNA cassette described in the above item <30>, wherein the DNA (b) is a DNA specified in the above item <11>.

<32> The plasmid or the DNA cassette described in any one of the above items <28> to <31>, wherein the protein (A) or (B) is a protein which recognizes DNA ends generated by DNA double strand break, and binds to the DNA ends recognized to recruit DNA-dependent kinase to the DNA ends.

<33> A method of preparing a transformant by using the alga described in any one of the above items <14> to <22> as a host, which contains performing arbitrary modification by homologous recombination in a targeted site of genomic DNA of the alga.

<34> The method of preparing the transformant described in the above item <33>, wherein an arbitrary gene is incorporated into a targeted site of genomic DNA by homologous recombination.

<35> The method of preparing the transformant described in the above item <33>, wherein an arbitrary gene is disrupted by homologous recombination.

EXAMPLES

Hereinafter, the present invention will be described more in detail with reference to Examples, but the present invention is not limited thereto. Herein, the nucleotide sequences of the primers used in Examples are shown in Table 1.

TABLE 1

| Primer No | Sequence | SEQ ID NO |
|---|---|---|
| 2 | ccctccgagcagattatggccaagctgaccagcgccgttccggtgctc | 2 |
| 3 | ctcttccacagaagcttagtcctgctcctcggccacgaagtgcacgcag | 3 |
| 4 | ggcggtcttttgtcctttcctctatagcccgc | 4 |
| 5 | aatctgctcggaggggaggatcaagggaaag | 5 |
| 6 | gcttctgtggaagagccagtggtagtagcagtagc | 6 |
| 7 | ctgatcttgtccatctcgtgtgccacgggtggca | 7 |
| 10 | ggacaaaagaccgccagctgtttcctgtgtgaaattgttatccgctc | 10 |
| 11 | gatggacaagatcagttaagccagccccgacacccgccaacaccgctg | 11 |
| 12 | acacaggaaacagcttagctatccatcttgtcctg | 12 |
| 13 | ggacaaaagaccgccaccttaaatgcaattccttg | 13 |
| 14 | gatggacaagatcagagcagcccttcgaactagac | 14 |
| 15 | tcggggctggcttaaggcacatgtttatgcctgtc | 15 |
| 19 | agctgtttcctgtgtgaaattgttatccgctc | 19 |
| 20 | ttaagccagccccgacacccgccaacaccgctg | 20 |
| 21 | tagctatccatcttgtcctggtacactgtc | 21 |
| 22 | ggcacatgtttatgcctgtcctcgaccggac | 22 |
| 23 | tagctatccatcttgtcctg | 23 |
| 24 | gtcttcttttctttggagtg | 24 |
| 26 | ccctccgagcagattatggtcgagattcgaagcatggacgatgcg | 26 |
| 27 | ctcttccacagaagctcagaagaactcgtccaacagccggtaaaac | 27 |
| 28 | acacaggaaacagctgaatgcatgccggccgagaa | 28 |
| 29 | ggacaaaagaccgccggagcaggacagaatgggct | 29 |
| 30 | gatggacaagatcagtgcggggatgccaaagatct | 30 |
| 31 | tcggggctggcttaagtttcaggcggtggaaagcg | 31 |
| 35 | acacaggaaacagctaactcggcgcacccaaaaag | 35 |
| 36 | ggacaaaagaccgccacccaccaacgtcccctttt | 36 |
| 37 | gatggacaagatcaggacgggcatgattgtgatgg | 37 |
| 38 | tcggggctggcttaatgtggcagcactgtgtctta | 38 |
| 42 | gaatgcatgccggccgagaa | 42 |
| 43 | gtttcaggcggtggaaagcg | 43 |
| 44 | aactcggcgcacccaaaaag | 44 |
| 45 | tgtggcagcactgtgtctta | 45 |
| 46 | atgtaccccagcttagc | 46 |
| 47 | tctttgcgctggaccctcg | 47 |
| 48 | atcgatgaaatcaatgtctg | 48 |
| 49 | gagcgactggccaaaagtac | 49 |

Example 1 Preparation of a Ku Gene-Disrupted Strain (Hereinafter, Also Referred to as "ΔKu Strain")

(1) Construction of Plasmid for Zeocin Resistance Gene Expression

A zeocin resistance gene (SEQ ID NO: 1) was artificially synthesized. Using the thus-synthesized DNA fragments as a template, and a pair of the primer Nos. 2 and 3 shown in Table 1, PCR was carried out, to amplify the zeocin resistance gene.

Further, using a genome of *Nannochloropsis oculata* strain NIES-2145 (obtained from National Institute for Environmental Studies (NIES)) as a template, and a pair of the primer Nos. 4 and 5, and a pair of the primer Nos. 6 and 7 shown in Table 1, respectively, PCRs were carried out to amplify the VCP1 promoter sequence (SEQ ID NO: 8) and the VCP1 terminator sequence (SEQ ID NO: 9).

Furthermore, using a plasmid vector pUC118 (manufactured by Takara Bio) as a template, and a pair of the primer Nos. 10 and 11 shown in Table 1, PCR was carried out to amplify the plasmid vector pUC118.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for zeocin resistance gene expression.

Herein, the expression plasmid consisted of the pUC118 vector sequence and an insert sequence in which the VCP1 promoter sequence, the zeocin resistance gene and the VCP1 terminator sequence were linked in this order.

(2) Construction of Plasmid for Homologous Recombination of Endogenous Ku Gene in *Nannochloropsis*

Using genomic DNA extracted from *Nannochloropsis oculata* strain NIES-2145 as a template, and pairs of the primer Nos. 12 and 13, and the primer Nos. 14 and 15, shown in Table 1, PCRs were carried out to amplify the partial sequences (genome sequence (A) (the nucleotide sequence of the $1120^{th}$ to $2650^{th}$ nucleotides set forth in SEQ ID NO: 16 (SEQ ID NO: 17)), and genome sequence (B) (the nucleotide sequence of the $2930^{th}$ to $4520^{th}$ nucleotides set forth in SEQ ID NO: 16 (SEQ ID NO: 18))) of the genome sequence around the Ku gene (SEQ ID NO: 16), shown in FIG. 1(*a*).

Further, using the plasmid for the zeocin resistance gene expression, and a pair of the primer Nos. 4 and 7 shown in Table 1, PCR was carried out to obtain a fragment of a cassette for the zeocin resistance gene expression (Pvcp1-ble-Tvcp1).

Furthermore, using the plasmid vector pUC118 as a template, and a pair of the primer Nos. 19 and 20 shown in Table 1, PCR was carried out to amplify the plasmid vector pUC118.

These amplified fragments were treated by restriction enzyme DpnI respectively, and were purified using the High Pure PCR Product Purification Kit.

After that, the plasmid for homologous recombination of the Ku gene (hereinafter, also referred to as "plasmid for Ku gene KO") was constructed by fusing the obtained fragment of genome sequence (A), the fragment of genome sequence (B), the fragment of the cassette for zeocin resistance gene expression, and the plasmid vector pUC118, by using In-Fusion HD Cloning Kit.

Figure 1B:
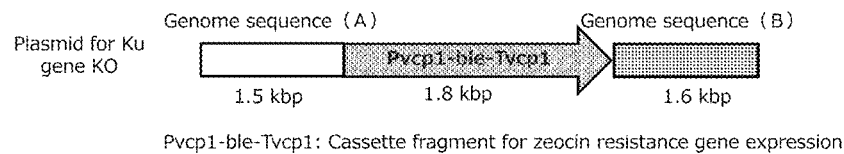

Herein, the plasmid consisted of the pUC118 vector sequence and an insert sequence (see FIG. 1(b)) in which the upstream genome sequence of the sequence set forth in SEQ ID NO: 16 (genome sequence (A), SEQ ID NO: 17), the VCP1 promoter sequence, the zeocin resistance gene, the VCP1 terminator sequence, and the downstream genome sequence of the sequence set forth in SEQ ID NO: 16 (genome sequence (B), SEQ ID NO: 18) were linked in this order.

(3) Introduction of a Cassette for Homologous Recombination of the Ku Gene into *Nannochloropsis oculata*

Using the above-described plasmid for homologous recombination of the Ku gene as a template, and a pair of the primer Nos. 21 and 22 shown in Table 1, PCR was carried out to amplify a cassette for homologous recombination of the Ku gene (an insertion sequence shown in FIG. 1(b)).

The amplified DNA fragment was purified using High Pure PCR Product Purification Kit. Herein, sterilized water was used for elution upon purification without using an elution buffer included in the kit.

About $1 \times 10^8$ cells of *Nannochloropsis oculata* strain NIES-2145 were washed with 384 mM sorbitol solution to completely remove a salt, and the resultant was used as a host cell for transformation. The cassette for homologous recombination of the Ku gene was mixed by about 500 ng with the host cell, and electroporation was carried out under the conditions of 50 μF, 500 Ω and 2,200 v/2 mm.

Recovery cultivation was performed for 24 hours in a media in which a nitrogen concentration in f/2 liquid medium (75 mg of $NaNO_3$, 6 mg of $NaH_2PO_4 \cdot 2H_2O$, 0.5 μg of vitamin B12, 0.5 μg of biotin, 100 μg of thiamine, 10 mg of $Na_2SiO_3 \cdot 9H_2O$, 4.4 mg of $Na_2EDTA \cdot 2H_2O$, 3.16 mg of $FeCl_3 \cdot 6H_2O$, 12 μg of $CoSO_4 \cdot 7H_2O$, 21 μg of $ZnSO_4 \cdot 7H_2O$, 180 μg of $MnCl_2 \cdot 4H_2O$, 7 μg of $CuSO_4 \cdot 5H_2O$, 7 μg of $Na_2MoO_4 \cdot 2H_2O$/artificial sea water 1 L) was reinforced 15 times, and a phosphorus concentration therein was reinforced 5 times (hereinafter, referred to as "N15P5 medium"). After that, the resultant was inoculated in N15P5 agar medium containing 2 μg/mL of zeocin, and cultured for two to three weeks under 12 h/12 h light-dark conditions at 25° C. under an atmosphere of 0.3% $CO_2$.

(4) Selection of ΔKu Strain

The ΔKu strain in which the Ku gene derived from *Nannochloropsis oculata* was deleted by the cassette for homologous recombination was selected, by PCR, from among the colonies obtained.

Figure 2A:
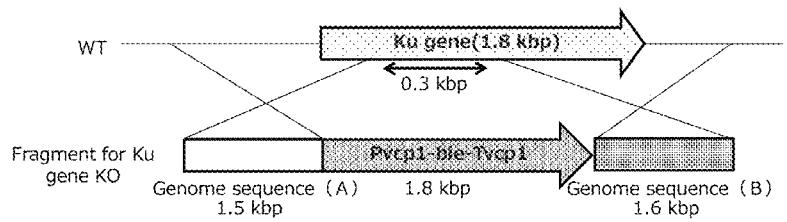
FIG. 2(*a*) is a diagram schematically showing a method of preparing a deficient strain of a gene encoding the protein (A) or (B), using a cassette for homologous recombination.

As shown in FIG. 2(a), the ΔKu strain was prepared by causing homologous recombination between the genomic DNA of the wild-type (WT) strain and the cassette for homologous recombination of the Ku gene (fragments for Ku gene KO) to incorporate the cassette for homologous recombination of the Ku gene into the genomic DNA.

Figure 2B:
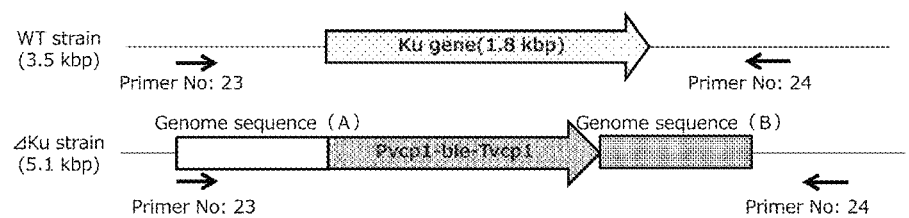

The ΔKu strain was selected by performing PCR by using a pair of the primer Nos. 23 and 24 shown in Table 1, and applying a difference in lengths of fragments to be amplified as an indicator (see FIG. 2(b)).

Example 2 Suppression of Non-Homologous End-Joining Repair Using ΔKu Strain and Examination of Probability of Acquiring Transformant in which Homologous Recombination Occurred (1) Construction of Plasmid for Paromomycin Resistance Gene Expression Using a paromomycin resistance gene (SEQ ID NO: 25) artificially synthesized as a template, and a pair of the primer Nos. 26 and 27 shown in Table 1, PCR was carried out to obtain the paromomycin resistance gene.

The amplified fragment was purified by a method in a manner similar to that in Example 1, and then the plasmid for paromomycin resistance gene expression was constructed by fusing the paromomycin resistance gene, the VCP1 promoter sequence, the VCP1 terminator sequence and the plasmid vector pUC118 by using the In-Fusion HD Cloning Kit.

Herein, the expression plasmid consisted of the pUC118 vector sequence and an insert sequence in which the VCP1 promoter sequence, the paromomycin resistance gene and the VCP1 terminator sequence were linked in this order.

Figure 3A:
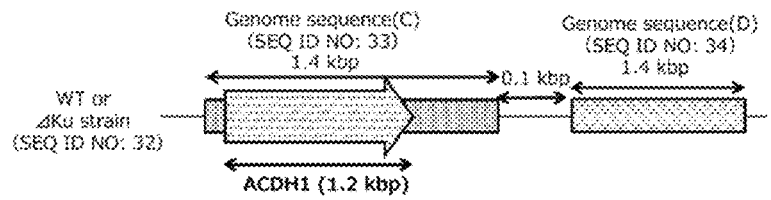
FIG. 3(*a*) is a diagram schematically showing a genome sequence around one kind of genes encoding acyl-CoA dehydrogenases (hereinafter, also referred to as "ACDH1 gene") in a wild-type strain of *Nannochloropsis oculata* or a deficient strain of the gene encoding the protein (A) or (B).

(2) Construction of Plasmid for Homologous Recombination Targeting a Gene Encoding Acyl-CoA Dehydrogenase Using the genomic DNA extracted from *Nannochloropsis oculata* strain NIES-2145 as a template, and pairs of the primer Nos. 28 and 29, and the primer Nos. 30 and 31, shown in Table 1, PCRs were carried out to amplify the partial sequences (genome sequence (C) (the nucleotide sequence of the $101^{st}$ to 1550th nucleotides set forth in SEQ ID NO: 32 (SEQ ID NO: 33)), and genome sequence (D) (the nucleotide sequence of the $1661^{st}$ to $3100^{th}$ nucleotides set forth in SEQ ID NO: 32 (SEQ ID NO: 34))) of the genome sequence around the ACDH1 gene (SEQ ID NO: 32), shown in FIG. 3(a).

Figure 4A:
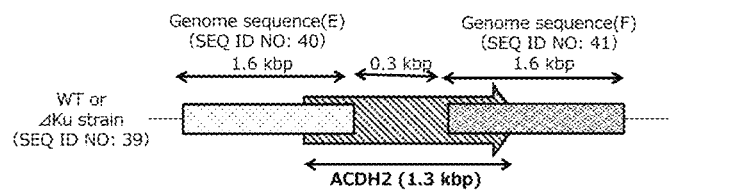
FIG. 4(*a*) is a diagram schematically showing a genome sequence around one kind of genes encoding acyl-CoA dehydrogenases (hereinafter, also referred to as "ACDH2 gene") different from the gene shown in FIG. 3(*a*), in a wild-type strain of *Nannochloropsis oculata* or a deficient strain of the gene encoding the protein (A) or (B).

Similarly, using pairs of the primer Nos. 35 and 36, and the primer Nos. 37 and 38, shown in Table 1, PCRs were carried out to amplify the partial sequences (genome sequence (E) (the nucleotide sequence of the $111^{st}$ to $1700^{th}$ nucleotides set forth in SEQ ID NO: 39 (SEQ ID NO: 40)), and genome sequence (F) (the nucleotide sequence of the $1951^{st}$ to $3500^{th}$ nucleotides set forth in SEQ ID NO: 39 (SEQ ID NO: 41))) of the genome sequence around the ACDH2 gene (SEQ ID NO: 39), shown in FIG. 4(a).

Furthermore, using the plasmid for the paromomycin resistance gene expression as a template, and a pair of the primer Nos. 4 and 7 shown in Table 1, PCR was carried out to obtain a fragment of a cassette for the paromomycin resistance gene expression.

The amplified fragments were purified respectively by a method in a manner similar to that in Example 1, and then, a plasmid for homologous recombination of the ACDH1 gene was constructed by fusing the obtained fragment of the genome sequence (C), the fragment of the genome sequence (D), the fragment of the cassette for the paromomycin resistance gene expression, and the plasmid vector pUC118 by using In-Fusion HD Cloning Kit. Similar to that described above, a plasmid for homologous recombination of the ACDH2 gene was constructed by fusing the fragment of genome sequence (E), the fragment of genome sequence (F), the fragment of the cassette for paromomycin resistance gene expression, and the plasmid vector pUC118.

Figure 3B:
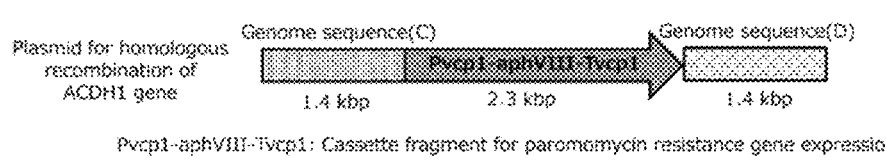
Figure 4B:
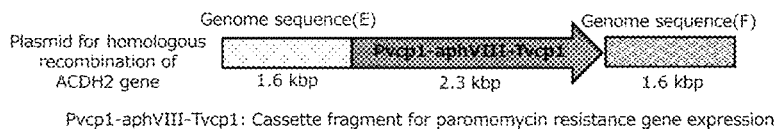

Herein, the plasmid consisted of the pUC118 vector sequence and an insert sequence (see FIG. 3(b) or FIG. 4(b)) in which the upstream DNA sequence of the each ACDH gene (the fragment of genome sequence (C) or the fragment of genome sequence (E)), the VCP1 promoter sequence, the paromomycin resistance gene, the VCP1 terminator sequence, and the downstream DNA sequence of the each ACDH gene (the fragment of genome sequence (D) or the fragment of genome sequence (F)) were linked in this order.

(3) Introduction of a Cassette for Homologous Recombination of the ACDH1 Gene, or a Cassette for Homologous Recombination of the ACDH2 Gene into *Nannochloropsis oculata*

Using the plasmid for homologous recombination of the ACDH1 gene as a template, and a pair of the primer Nos. 42 and 43 shown in Table 1, PCR was carried out to amplify a cassette for homologous recombination of the ACDH1 gene (an insert sequence shown in FIG. 3(b)).

Similar to that described above, using the plasmid for homologous recombination of the ACDH2 gene as a template, and a pair of the primer Nos. 44 and 45 shown in Table 1, PCR was carried out to amplify a cassette for homologous recombination of the ACDH2 gene (an insert sequence shown in FIG. 4(b)).

The each amplified fragment was purified by a method in a manner similar to that in Example 1, respectively.

Using a wild type (WT) strain of *Nannochloropsis oculata* strain NIES-2145 or the ΔKu strain prepared in Example 1 as a host, the each cassette was introduced into the host by electroporation by a method in a manner similar to that in Example 1. After recovery cultivation, the resultant was inoculated in N15P5 agar medium containing 300 μg/mL of paromomycin, and cultured for two to three weeks under 12 h/12 h light-dark conditions at 25° C. under an atmosphere of 0.3% $CO_2$. And then, the colony was selected by using an indicator of the paromomycin resistance.

(4) Examination of Probability of Acquiring Transformant in which Homologous Recombination Occurred Strains in which homologous recombination occurred in a desired position on the genome by the cassette for homologous recombination were selected, by PCR, from among the colonies obtained, respectively, by targeting the ACDH1 gene or the ACDH2 gene of the *Nannochloropsis oculata*.

Figure 5A:
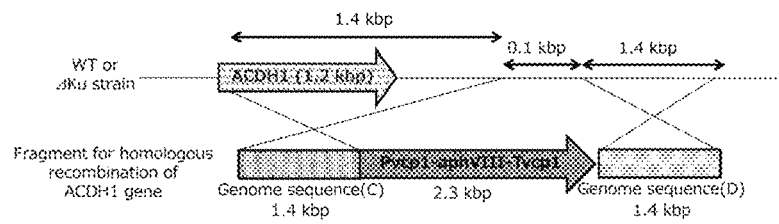
FIG. 5(*a*) is a diagram schematically showing a method of preparing a homologous recombinant strain of genome around an ACDH1 gene, using a cassette for homologous recombination of the ACDH1 gene.
Figure 5B:
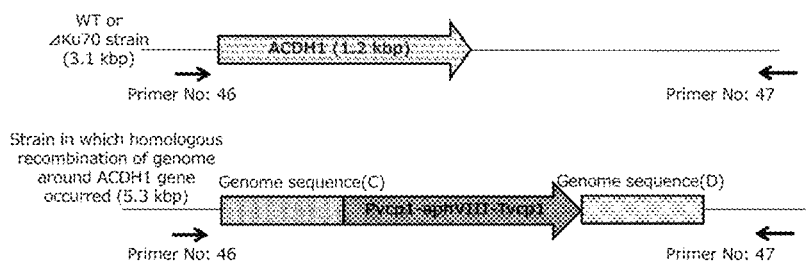

As shown in FIG. 5(a), the homologous recombination strain of genome around the ACDH1 gene was prepared by causing homologous recombination between the genomic DNA of the wild-type (WT) strain or the ΔKu strain and the cassette for homologous recombination of the ACDH1 gene (fragment for homologous recombination of the ACDH1 gene) to incorporate the cassette for homologous recombination of the ACDH1 gene into the genomic DNA. The homologous recombinant strain of genome around the ACDH1 gene was selected by performing PCR by using a pair of the primer Nos. 46 and 47 shown in Table 1, and applying a difference in lengths of fragments to be amplified as an indicator (see FIG. 5(b)).

Figure 6A:
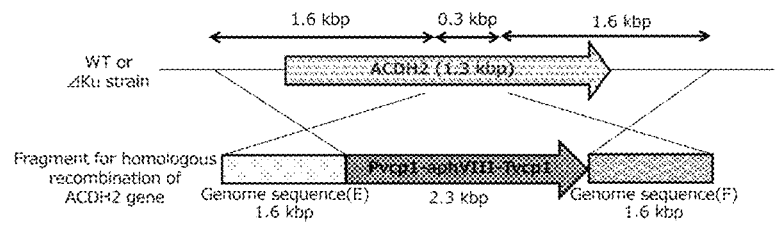
FIG. 6(a) is a diagram schematically showing a method of preparing a homologous recombinant strain of genome around an ACDH2 gene, using a cassette for homologous recombination of the ACDH2 gene.
Figure 6B:
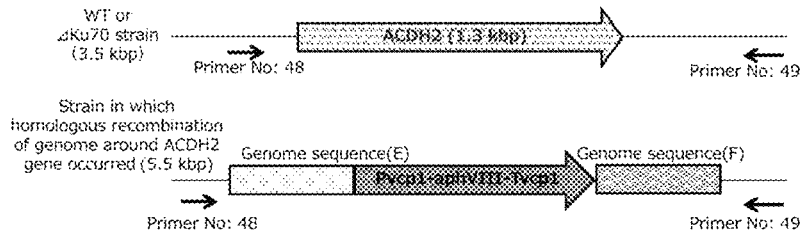
FIG. 6(b) is a schematic diagram for comparing sizes of DNA fragments to be amplified for confirming introduction of a cassette for homologous recombination between a wild-type strain of Nannochloropsis oculata or a deficient strain of the gene encoding the protein (A) or (B) and the homologous recombinant strain of genome around the ACDH2 gene.

As shown in FIG. 6(a), the homologous recombinant strain of genome around the ACDH2 gene was prepared by causing homologous recombination between the genomic DNA of the wild-type (WT) strain or the ΔKu strain and the cassette for homologous recombination of the ACDH2 gene (fragment for homologous recombination of the ACDH2 gene) to incorporate the cassette for homologous recombination of the ACDH2 gene into the genomic DNA. The homologous recombinant strain of genome around the ACDH2 gene was selected by performing PCR by using a pair of the primer Nos. 48 and 49 shown in Table 1, and applying a difference in lengths of fragments to be amplified as an indicator (see FIG. 6(b)).

According to the above-described procedure, homologous recombination efficiency was calculated according to the following formula, from the number of strains in which homologous recombination occurred in a genome site of a targeted ACDH gene by homologous recombination among the transformants acquired by applying paromomycin resistance as an indicator. Table 2 shows the results.

(Homologous recombination frequency)={(number of strains in which homologous recombination occurred)/(number of transformants having paromomycin resistance)}×100(%)

TABLE 2

| Host | | Homologous recombination frequency | |
|---|---|---|---|
| | | ACDH1 gene | ACDH2 gene |
| WT strain | line 1 | 5% (2/42) | — |
| | line 2 | 22% (4/18) | 13% (6/48) |
| ΔKu strain | line 1 | 100% (5/5) | 100% (12/12) |
| | line 2 | 100% (13/13) | 100% (17/17) |

As shown in Table 2, it became apparent that homologous recombination frequency is significantly higher in the ΔKu strain, as compared with the WT strain, without depending on a gene position in which homologous recombination is performed.

From the results described above, probability of acquiring the transformant in which homologous recombination occurs can be significantly improved by suppressing, inhibiting or deleting function of NoKu in algae belonging to the genus *Nannochloropsis*.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2016-237757 filed in Japan on Dec. 7, 2016, which is entirely herein incorporated by reference.

What is claimed is:

1. A method of producing a transformant, the method comprising:
   transforming a *Nannochloropsis* host with a polynucleotide and inserting the polynucleotide at a target site in the host's genomic DNA by homologous recombination;
   wherein, in the host:
   a gene encoding the following protein (A) or protein (B) has been deleted or inactivated prior to the transforming, thereby
   (i) reducing the host's frequency of non-homologous recombination, and
   (ii) increasing the host's frequency of homologous recombination;
   wherein, both (i) and (ii) are as compared to that of a *Nannochloropsis* alga that is the same as the host except that the gene encoding protein (A) or protein (B) is not deleted or inactivated:
   wherein protein (A) is:
   (A) a protein consisting of the amino acid sequence set forth in SEQ ID NO: 50; and
   wherein protein (B) is:
   (B) a DNA binding protein consisting of an amino acid sequence having 90% or more identity with the amino acid sequence of protein (A),
   and wherein protein (B) recognizes DNA ends generated by a DNA double strand break, and binds to the DNA ends recognized to recruit a DNA-dependent kinase to the DNA ends.

2. A method of producing a host, the method comprising deleting or inactivating a gene that encodes the following protein (A) or protein (B) in an alga belonging to the genus *Nannochloropsis*, thereby producing a host in which the host's frequency of non-homologous recombination is reduced and the host's frequency of homologous recombination is increased, both as compared to that of a *Nannochloropsis* alga that is the same as the host except that the gene encoding protein (A) or encoding protein (B) is not deleted or inactivated:
   wherein protein (A) is:
   (A) a protein consisting of the amino acid sequence set forth in SEQ ID NO: 50; and
   wherein protein (B) is:
   (B) a DNA binding protein consisting of an amino acid sequence having 90% or more identity with the amino acid sequence of protein (A),
   and wherein protein (B) recognizes DNA ends generated by a DNA double strand break, and binds to the DNA ends recognized to recruit a DNA-dependent kinase to the DNA ends.

3. The method according to claim 1, wherein the gene encoding protein (A) or the gene encoding protein (B) is deleted.

4. The method according to claim 1, wherein the amino acid sequence of protein (B) has 95% or more identity with the amino acid sequence of protein (A).

5. The method according to claim 1, wherein the gene encoding protein (A) is a gene consisting of the following DNA (a) or the gene encoding protein (B) is a gene consisting of the following DNA (b):
   wherein DNA (a) is:
   (a) a DNA consisting of the nucleotide sequence set forth in SEQ ID NO: 51; and
   wherein DNA (b) is:
   (b) a DNA consisting of a nucleotide sequence having 85% or more identity with the nucleotide sequence of DNA (a), and encoding the protein (B).

6. The method according to claim 1, wherein the host is *Nannochloropsis oculata*.

7. An alga belonging to the genus *Nannochloropsis*, in which
   (a) a gene encoding the following protein (A) or protein (B) is deleted or inactivated; and
   (b) the alga's frequency of non-homologous recombination is reduced and the alga's frequency of homologous recombination is increased, both as compared to that of a *Nannochloropsis* alga that is the same except that the gene encoding protein (A) or the gene encoding protein (B) is not deleted or inactivated, wherein protein (A) is:
(A) a protein consisting of the amino acid sequence set forth in SEQ ID NO: 50; and
wherein protein (B) is:
(B) a DNA binding protein consisting of an amino acid sequence having 90% or more identity with the amino acid sequence of protein (A), and wherein protein (B) is a protein that recognizes DNA ends generated by a DNA double strand break, and binds to the DNA ends recognized to recruit a DNA-dependent kinase to the DNA ends.

8. The alga according to claim 7, wherein the gene encoding protein (A) or the gene encoding protein (B) is deleted.

9. The alga according to claim 7, wherein the amino acid sequence of protein (B) has 95% or more identity with the amino acid sequence of protein (A).

10. The alga according to claim 7, wherein the gene encoding protein (A) is a gene consisting of the following DNA (a) or the gene encoding protein (B) is a gene consisting of the following DNA (b):
wherein DNA (a) is:
(a) a DNA consisting of the nucleotide sequence set forth in SEQ ID NO: 51; and
wherein DNA (b) is:
(b) a DNA consisting of a nucleotide sequence having 85% or more identity with the nucleotide sequence of DNA (a), and encoding the protein (B).

11. The alga according to claim 7, wherein the alga is *Nannochloropsis oculata*.

12. The method according to claim 2, wherein the gene encoding protein (A) or protein (B) is deleted.

13. The method according to claim 2, wherein the amino acid sequence of protein (B) has 95% or more identity with the amino acid sequence of protein (A).

14. The method according to claim 2, wherein the gene encoding protein (A) is a gene consisting of the following DNA (a) or the gene encoding protein (B) is a gene consisting of the following DNA (b):
wherein DNA (a) is:
(a) a DNA consisting of the nucleotide sequence set forth in SEQ ID NO: 51; and
wherein DNA (b) is:
(b) a DNA consisting of a nucleotide sequence having 85% or more identity with the nucleotide sequence of DNA (a), and encoding the protein (B).

15. The method according to claim 2, wherein the alga is *Nannochloropsis oculata*.

* * * * *